US006180349B1

(12) United States Patent
Ginzinger et al.

(10) Patent No.: US 6,180,349 B1
(45) Date of Patent: Jan. 30, 2001

(54) QUANTITATIVE PCR METHOD TO ENUMERATE DNA COPY NUMBER

(75) Inventors: David G. Ginzinger, San Francisco, CA (US); Tony E. Godfrey, Pittsburgh, PA (US); Ronald H. Jensen, Livermore; Joe W. Gray, San Francisco, both of CA (US)

(73) Assignee: The Regents of the University of California, Oakland, CA (US)

( * ) Notice: Under 35 U.S.C. 154(b), the term of this patent shall be extended for 0 days.

(21) Appl. No.: 09/314,246

(22) Filed: May 18, 1999

(51) Int. Cl.[7] .............................. C07H 21/02; C07H 21/04
(52) U.S. Cl. .............................. 435/6; 536/23.1; 536/24.3
(58) Field of Search ................................. 435/6, 91.2, 5; 707/500; 536/24.3, 24.31, 23.1

(56) References Cited

U.S. PATENT DOCUMENTS

| 5,210,015 | 5/1993 | Gelfand et al. . |
| 5,219,727 | 6/1993 | Wang et al. . |
| 5,538,848 | 7/1996 | Livak et al. . |
| 5,863,736 | 1/1999 | Haaland . |
| 5,876,930 | 3/1999 | Livak et al. . |

OTHER PUBLICATIONS

Glatt et al., "The human gamma–aminobutyric acid receptor subunit beta–3 and alpha–5 gene cluster in chromosome 15q11–q13 is rich in highly polymorphic (CA)n Repeats," Genomics, vol. 19, pp 157–160, 1994.*

Lai et al., "Usefulness of dinucleotide polymorphism markers in genetic analysis of Duchenne's muscular dystrophy cases in Singapore," Southeast Asian Journal of Tropical Medicine and Public Health, vol. 26, Suppl 1, pp. 175–178, 1995.*

Holland, Pamela M.; Abramson, Richard D.; Watson, Robert and Gelfand, David H.; Detection of specific polymerase chain reaction by utilizing the 5'→3' exonuclease activity of *Thermus aquaticus* DNA polymerase, *Proc. Natl. Acad. Sci. USA*, Aug. 1991, vol. 88, pp. 7276–7280.

Livak, K.J.; Flood, Susan J. A.; Marmaro, Jeffrey; Giusti, William and Deetz, Karin; Oligonucleotides with Fluorescent Dyes at Opposite Ends Provide a Quenched Probe System Useful for Detecting PCR Product and Nuclei Acid Hybridization, *PCR Methods and Applications*, vol. 4, pp. 357–362, 1995.

Heid, Christian A.; Stevens, Junko; Livak, Kenneth J. and Williams, P. Mickey; Real Time Quantitative PCR, *Genome Research*, vol. 6, pp. 986–994, 1996.

Gibson, Ursula E. M.; Heid, Christian A. and Williams, P. Mickey; A Novel Method for Real Time Quantitative RT–PCR, *Genome Research*, vol. 6, pp. 995–1001, 1996.

* cited by examiner

Primary Examiner—John S. Brusca
Assistant Examiner—Young Kim
(74) Attorney, Agent, or Firm—Townsend and Townsend and Crew LLP

(57) ABSTRACT

The present invention provides rapid and inexpensive methods for determining the copy number of a test locus of interest. The methods generally involve monitoring the formation of amplification product using real time amplification detection systems to quantify the amount of test locus and reference loci in a test subject and the amount of test locus and reference loci in at least one control subject. The methods can be used to interrogate the copy number of loci containing simple sequence repeats. Since such sequences are ubiquitous in eukaryotic genomes, the present methods have wide-ranging applicability. The methods of the present invention can be used as diagnostic and prognostic tools and in correlating abnormal copy number values for specific loci with disease and effectiveness of different treatment options.

45 Claims, 7 Drawing Sheets

US 6,180,349 B1

QUANTITATIVE PCR METHOD TO ENUMERATE DNA COPY NUMBER

FIELD OF THE INVENTION

The present invention relates to the field of nucleic acid chemistry and, more particularly, to methods of quantifying the copy number of a locus of interest. The present methods allow for rapid screening of samples to determine copy number, hence the methods can be used in various clinical applications including, establishing correlations between copy number and pathology, and rapidly screening patients to identify those having a disease or those which are susceptible to acquiring a disease.

BACKGROUND OF THE INVENTION

In a variety of different fields of biological research, methods for quantitating nucleic acid sequences has become an increasingly important tool. For example, measurement of gene expression has been used in several different applications to monitor biological responses to various stimuli. An important step in the molecular genetic analysis of human disease, especially cancer and tumors, is often the enumeration of DNA copy number in particular regions of the genome.

Several different approaches are currently available to make quantitative determinations of nucleic acids. Chromosome-based techniques, such as comparative genomic hybridization (CGH) and fluorescent in situ hybridization (FISH) facilitate efforts to cytogenetically localize genomic regions that are altered in tumor cells. Regions of genomic alteration can be narrowed further using loss of heterozygosity analysis (LOH), in which tumor DNA is analyzed and compared with normal DNA for the loss of a heterozygous polymorphic marker. The first experiments used restriction fragment length polymorphisms (RFLPs) (1, 2), or hypervariable minisatellite DNA (3). In recent years LOH has been performed primarily using PCR amplification of microsatellite markers and electrophoresis of the radiolabeled (4) or fluorescently labeled PCR products (5, 6) and compared between paired normal and tumor DNAs.

These chromosomal methods, however, have several shortcomings. For example, LOH, requires heterozygosity at the markers being analyzed and it is not possible to differentiate between deletions and amplifications with the method. Both FISH and LOH are slow and labor intensive. CGH is an excellent tool for scanning the whole genome, but it is limited to 5 Mb resolution at best.

A number of other methods have also been developed to quantify nucleic acids (Southern, E. M., J. Mol. Biol., 98:503–517, 1975; Sharp, P. A., et al., Methods Enzymol. 65:750–768, 1980; Thomas, P. S., Proc. Nat. Acad. Sci., 77:5201–5205, 1980). More recently, PCR and RT-PCR methods have been developed which are capable of measuring the amount of a nucleic acid in a sample. One approach, for example, measures PCR product quantity in the log phase of the reaction before the formation of reaction products plateaus (Kellogg, D. E., et al., Anal. Biochem. 189:202–208 (1990); and Pang, S., et al., Nature 343:85–89 (1990)). A gene sequence contained in all samples at relatively constant quantity is typically utilized for sample amplification efficiency normalization. This approach, however, suffers from several drawbacks. The method requires that each sample have equal input amounts of the nucleic acid and that the amplification efficiency between samples be identical until the time of analysis. Furthermore, it is difficult using the conventional methods of PCR quantitation such as gel electrophoresis or plate capture hybridization to determine that all samples are in fact analyzed during the log phase of the reaction as required by the method.

Another method called quantitative competitive (QC)-PCR, as the name implies, relies on the inclusion of an internal control competitor in each reaction (Becker-Andre, M., Meth. Mol. Cell Biol. 2:189–201 (1991); Piatak, M. J., et al., BioTechniques 14:70–81 (1993); and Piatak, M. J., et al., Science 259:1749–1754 (1993)). The efficiency of each reaction is normalized to the internal competitor. A known amount of internal competitor is typically added to each sample. The unknown target PCR product is compared with the known competitor PCR product to obtain relative quantitation. A difficulty with this general approach lies in developing an internal control that amplifies with the same efficiency of the target molecule.

Another problem common to a variety of PCR quantitation methods is that probes must be tailored for each locus to be interrogated. Yet another shortcoming is that often a single locus or reference marker is used as a control. The risk inherent in methods relying on a single reference marker as a control is that the quantity of DNA may differ from the normal value, thus preventing a precise measurement of the locus being tested. This is of particular concern in the case of studies with tumors because genomic instability is a common feature of tumors. Current methods also lack the precision necessary to consistently distinguish between one and two copies of DNA.

SUMMARY OF THE INVENTION

The present invention provides rapid and inexpensive methods for determining the copy number of essentially any region of a genome, especially the genome of an eukaryote. The methods generally involve monitoring the formation of amplification product using real time amplification detection systems to quantify the amount of test locus and reference loci in a test subject and the amount of test locus and reference loci in at least one control subject. The methods can be used to interrogate the copy number of loci containing simple sequence repeats. Since such sequences are ubiquitous in eukaryotic genomes, the present methods have wide-ranging applicability. The methods of the present invention can be used as diagnostic and prognostic tools and in correlating abnormal copy number values for specific loci with disease and effectiveness of different treatment options.

In certain methods, the determination of copy number for a polynucleotide locus in a sample includes four steps. First, a test polynucleotide locus in a nucleic acid sample from a test subject is amplified to determine a value for the quantity of the test locus in the sample from the test subject. Second, a plurality of reference polynucleotide loci in a second nucleic acid sample from the test subject are amplified to determine a value for the quantity of the reference loci in a second sample from the test subject. Third, the test polynucleotide locus from a control subject is amplified to determine a value for the quantity of the test locus in the sample from the control subject. Finally, a plurality of reference polynucleotide loci from a second nucleic acid sample from the control subject is amplified to determine a value for the quantity of the reference loci in the second sample from the control subject. The values determined in these four steps are then utilized to determine a measure of the copy number of the test locus in the sample from the test subject.

In some instances, the four values just described, i.e., the values for the test locus and reference loci in the test subject and control subject, are values for the extent of amplification necessary for amplification product formed from the test locus or reference loci to reach a threshold value. Thus, in such methods, the value for the test locus in the test subject is a value for the extent of amplification required for amplification product of the test locus to reach a threshold level; likewise, the value for the reference loci in the test subject is a value for the extent of amplification required for amplification product of the reference loci to reach the threshold level. Similarly, for the control subject, the value for the test locus in the control subject is a value for the extent of amplification required for amplification product of the test locus in the control subject to reach the threshold level, and the value for the reference loci in the control subject is a value for the extent of amplification required for amplification product of the reference loci in the control subject to reach a threshold level. In some methods, the values for the extent of amplification required to reach a threshold level are Ct values, or the number of amplification cycles required for the amount of amplification product to reach a threshold level. In general, however, the values for the test locus and the reference loci in the test subject and control subject can be any value which is a measure of the rate of amplification product formation, or a value which is a measure of the time required for a certain amount of amplification product to be formed.

In some methods, the values for the test locus and reference loci in the control subject are predetermined values. In these instances, the methods for measuring the copy number of a polynucleotide locus in a sample involves only two amplification steps, in order to determine values for the quantity of test locus and reference loci in the test subject. In the calculation of copy number of the test locus for the test subject, the predetermined values for the test locus and the reference loci in the control subject are still used.

More specifically, such methods include amplifying a test polynucleotide locus in a nucleic acid sample from a test subject and determining a value for the quantity of the test locus in the sample from the test subject. A plurality of control polynucleotide loci in a second nucleic acid sample from the test subject are amplified to determine a value for the quantity of reference loci in the second sample from the test subject. A measure of the copy number of the test locus in the sample from the test subject is then determined from these two measured values for the test subject and from the predetermined values for the test locus and reference loci in the control subject, wherein the value for the test locus in the control subject is a value for the quantity of the test locus in a sample from a control subject, and wherein the value for the reference loci in the control subject is a value for the quantity of the reference loci in a second sample from the control subject. As described above, the values for the test locus and reference loci in the test subject and control subject may be values for the extent of amplification necessary for the amplification products from the locus or loci to reach a threshold level.

For those methods in which the formation of amplification products is monitored, the amplification products can be monitored using any of a variety of real time amplification methods. For example, certain methods involve monitoring the formation of amplification products directly using labels which bind to the amplification product to form a complex that creates a detectable signal. Alternatively, the formation of amplification products can be monitored using probes which are complementary to the amplification products. During the extension phase of the amplification process, alteration of the probe generates a detectable signal which correlates with the formation of amplification product. Fluorogenic nuclease assays such as the "TaqMan" assay exemplify this type of approach, wherein a probe is used to monitor amplification product formation.

In some methods, the target locus and the reference loci comprise a simple sequence repeat such as a CA repeat. By using probes complementary to such simple sequence repeats, it is possible to interrogate essentially any region of the genome given the wide spread occurrence of such sequences throughout the genome.

DEFINITIONS

A "nucleic acid" is a deoxyribonucleotide or ribonucleotide polymer in either single or double-stranded form, including known analogs of natural nucleotides unless otherwise indicated.

A "polynucleotide" refers to a single or double-stranded polymer of deoxyribonucleotide or ribonucleotide bases.

A "probe" is an nucleic acid capable of binding to a target nucleic acid of complementary sequence through one or more types of chemical bonds, usually through complementary base pairing, usually through hydrogen bond formation, thus forming a duplex structure. The probe binds or hybridizes to a "probe binding site." A probe may include natural (i.e. A, G, C, or T) or modified bases (7-deazaguanosine, inosine, etc.). A probe can be an oligonucleotide which is a single-stranded DNA. Oligonucleotide probes can be synthesized or produced from naturally occurring polynucleotides. In addition, the bases in a probe can be joined by a linkage other than a phosphodiester bond, so long as it does not interfere with hybridization. Thus, probes may be peptide nucleic acids in which the constituent bases are joined by peptide bonds rather than phosphodiester linkages (see, for example, Nielsen et al., Science 254, 1497–1500 (1991)). Some probes may have leading and/or trailing sequences of noncomplementarity flanking a region of complementarity.

A "perfectly matched probe" has a sequence perfectly complementary to a particular target sequence. The probe is typically perfectly complementary to a portion (subsequence) of a target sequence. The term "mismatch probe" refer to probes whose sequence is deliberately selected not to be perfectly complementary to a particular target sequence.

A "primer" is a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term "primer site" refers to the area of the target DNA to which a primer hybridizes. The term "primer pair" means a set of primers including a 5' "upstream primer" that hybridizes with the 5' end of the DNA sequence to be amplified and a 3' "downstream primer" that hybridizes with the complement of the 3' end of the sequence to be amplified.

The term "substantially complementary" means that a primer or probe need not be exactly complementary to its target sequence; instead, the primer or probe need be only sufficiently complementary to selectively hybridize to its respective strand at the desired annealing site. A non-complementary base or multiple bases can be included within the primer or probe, so long as the primer or probe retains sufficient complementarity with its polynucleotide binding site to form a stable duplex therewith.

A "locus" refers to a specific segment of a nucleic acid that is the subject of analysis and is defined by a pair of flanking primers.

"Copy number" means the number of copies of a particular locus in the genome of a particular organism.

A "simple sequence repeat" refers to a section of DNA that is repeated. Typically, an individual repeat is 2 to 10 bp long and is repeated 10 to 100 times. A simple sequence repeat can be microsatellite sequence. An example of a simple sequence repeat is the CA repeat which occurs frequently in eukaryotic genomes. The number of repeats and the length of a CA repeat can vary widely, but typically a CA repeat is 40–60 bp and includes 20–30 repeats. Simple sequence repeats that occur less frequently in eukaryotic genomes than CA repeats include TA repeats and GA repeats.

BRIEF DESCRIPTION OF THE DRAWINGS

FIG. 3A is a map of BACs (bacterial artificial chromosomes) spanning over 1 Mb of chromosome 20q13. (13). The length of insert sequence in each BAC is indicated by the length of each line. FIG. 3B shows both DNA copy number data obtained using the methods of the present invention (symbols with dashed lines connecting them) and FISH data (solid bars—with cell line indicated in parentheses) from the cell lines MCF-7(◆) and SKBR3 (■). These cell lines show moderate to high level amplification in this region of the genome. FIG. 3C, like FIG. 3B, shows a similar comparison of DNA copy number from the cell lines HS578T (■), HBL100 (◆), and MDA361 (▲). These cell lines all have normal to low-level amplification of DNA copy number in this region of the genome.

FIG. 7A is an ideogram of mouse chromosome 2. FIGS. 7B and 7C are the plots of the red to green ratios for mice that demonstrate large losses of chromosome 2. FIG. 7D is a profile from a mouse that contains no measurable loses of chromosome 2.

DETAILED DESCRIPTION

I. General

Figure 1:
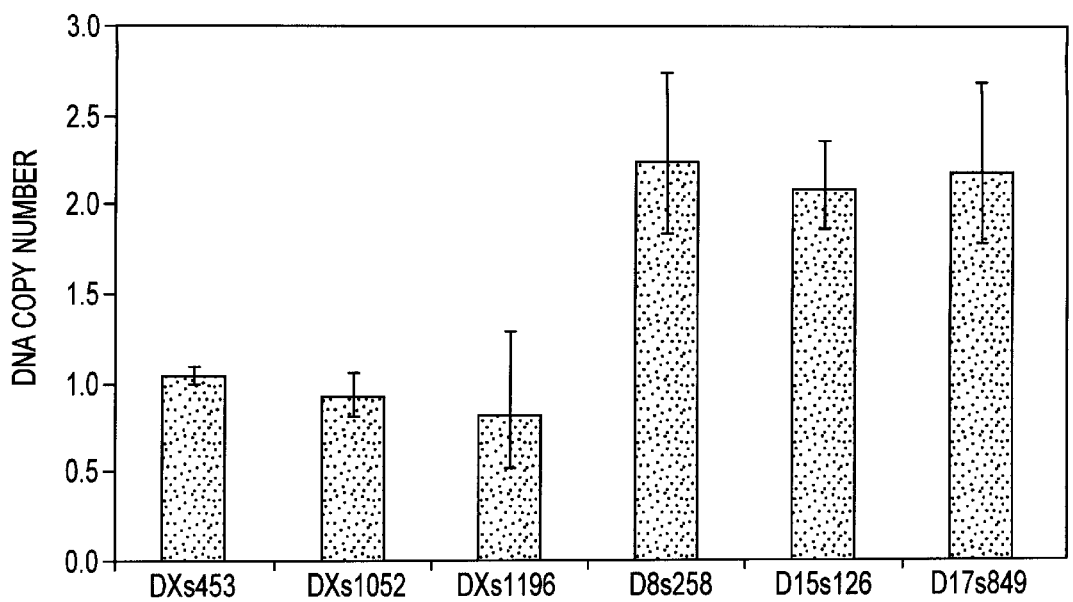
FIG. 1 depicts the DNA copy number of 3 loci on the X-chromosome and 1 locus on each of 3 autosomes of 4 males. The DNA for the control (i.e., the "calibrator") was 4 female DNAs. The relative DNA copy number of X-chromosomal markers is one compared to two DNA copies on autosomes in males as would be expected.

The present invention provides methods for measuring the copy number of a polynucleotide locus in a DNA sample. For any given segment of chromosomal DNA, normal individuals have two copies. One or more than two copies of a segment of DNA is abnormal and can be associated with disease. Thus, determination of copy number can aid in the prognosis and diagnosis of disease, as well as providing a means for establishing correlations between particular diseases and the copy number of certain loci or segments of DNA.

The methods of the present invention generally involve monitoring the formation of amplification product using real time amplification detection systems to quantify the amount of test locus and reference loci in a test subject and the amount of test locus and reference loci in at least one control subject. The test subject is the individual or organism for which a copy number determination is being made. The control subject is a normal individual for which there in no known increase in copy number for any particular locus.

Hence, the methods generally involve determining the copy number of a test locus in a test subject using four values: 1) a value for the quantity of a test locus in a test subject, 2) a value for the quantity of combined multiple reference loci in the test subject, 3) a value for the quantity of a test locus in a control subject and 4) a value for the quantity of combined multiple reference loci in a control subject. In general, the values used in the determinations of copy number are proportional to or correlated with the concentration of a nucleic acid segment defined by a particular test or control locus.

In certain methods, these four values are obtained by measuring the formation of amplification product generated during the amplification of the test locus and the reference loci. The formation of amplification products can be monitored using so called "real time" amplification methods. "Real time amplification" or "real time quantitative PCR" refer to amplification techniques, especially PCR, wherein the amount of amplification product formed can be monitored during the amplification process. A nonexhaustive list of such techniques include those described in references 12, and 15–17 and U.S. Pat Nos. 5,210,015 to Gelfand, 5,538, 848 to Livak, et al., and 5,863,736 to Haaland. These references are incorporated by reference in their entirety for all purposes. In some methods, the four values are more specifically correlated with the rate of formation of amplification products. It is possible to use real time measurements of amplification product because the rate of product formation is related to the original quantity of nucleic acid.

Some of the real time amplification methods utilized in the methods of the present invention utilize probes which bind to a segment of the region being amplified to monitor the formation of amplification products. Other methods, however, do not use probes but utilize various techniques to detect the amplification products themselves. For those methods utilizing probes, an alteration in the probe during the extension phase of amplification generates a detectable signal that is related to the formation of amplification product. Thus, this signal can be used to monitor amplification product formation. In some methods of the present invention, the probes are designed to be complementary to simple sequence repeats.

The methods of the present invention are broadly applicable to essentially any locus of interest. However, by interrogating loci which include simple sequence repeats (e.g., a CA repeat), it becomes possible using the methods of the present invention to interrogate the copy number of essentially any region in the genome because of the broad distribution of simple sequence repeats throughout eukaryotic genomes. Unlike other quantitation methods, heterozygosity at the locus being examined is not a prerequisite, hence all loci can be informative. By making measurements relative to combined multiple reference loci, the chance that an imbalance at the reference locus will alter the measurement for a test locus is greatly reduced.

With the methods of the present invention, correlations between variation in copy number for a test locus and the presence of, or susceptibility to, disease can be made. Such correlations or molecular pathology profiles enable clinicians to make more informed assessments regarding the prognosis for patients and more informed choices regarding which treatment options are likely to prove most beneficial for a particular patient. In cases in which the correlation between disease and variations in copy number has been previously established, the methods are useful as diagnostic tools to identify individuals susceptible to disease or whom have a disease. The methods can also be used in prenatal testing to identify DNA copy number abnormalities in a fetus.

II. Amplification Methods to Obtain Quantitative Measure of Loci in Test and Control Subjects A. General Approach In some methods of the present invention, the copy number of a polynucleotide locus in a sample is determined by amplifying a test locus and reference loci in both a test subject and at least one control subject and monitoring the rate of formation of amplification product generated from these loci. With such methods, a first value is determined by amplifying a test polynucleotide locus in a DNA sample obtained from a test subject and determining a value for the extent of amplification required for amplification product generated from the test locus to reach a threshold value or level. A second value is obtained by amplifying a plurality of reference polynucleotide loci in a second nucleic acid sample from the test subject and determining a value for the extent of amplification required for the amplification products of the reference loci to reach the threshold value.

The same general procedure is repeated with control samples. Thus, a third value is determined by amplifying the test polynucleotide locus in a nucleic acid in a first control sample for a control subject and determining a value for the extent of amplification required for amplification product of the test locus in the control subject to reach the threshold value. A fourth value is determined by amplifying a plurality of reference polynucleotide loci from a second nucleic acid sample from the control subject and determining a value for the extent of amplification required for the amplification products of the reference loci in the control subject to reach the threshold value. A measure of the copy number of the test locus in the sample from the test subject is then determined from these four values.

As described in greater detail below, the first and second sample from the test subject can be obtained from a common mixture; similarly, the first and second sample from the control subject can be obtained from a common mixture. The reference loci for the test subject and/or control subject can be amplified simultaneously by providing all the necessary primers during the amplification process.

In some methods, the values for the test locus in the control subject and the value for the reference loci in the control subjects are historical or predetermined values, i.e., the values for the control samples are determined at some point in time prior to the amplification reactions used to determine the values for the test locus and the reference loci in the test subject. In such instances, the amplification steps for the control subjects need not be performed; rather, the values previously determined for the control subjects can be used.

B. Test Subject/Control Subject

The test subject is the individual or organism for which a copy number determination is being performed. The control subject is a normal individual or organism that is not known to have an abnormal copy number at any region in the genome. Although a control subject typically refers to a single individual or organism, the control subject can instead include a sample which contains fragments of nucleic acid obtained from various sources which includes the appropriate loci.

C. Test Locus/Reference Loci

The test locus refers to the locus for which a copy number value is to be determined. The test locus to be interrogated with the methods of the present invention can be essentially any locus susceptible to copy number variation. All that is required is that sufficient sequence information is known or can be determined regarding the test locus so that the necessary primers for amplification can be obtained. Reference loci are loci which tend to show minimal variation in copy number from control individual to control individual, making the loci a good reference against which the copy number for the test locus can be compared.

Care is taken in the selection of all loci (i.e., test and reference loci). Since they serve as sensitive measures of copy number, all loci should exhibit only minor variations in copy number from control individual to control individual. As described in additional detail below, this can be assessed by determining a standard deviation for the copy number value determined for multiple control subjects. If the standard deviation exceeds that typically obtained for other loci measured on control individuals, that particular locus is not typically used in the methods of the present invention.

The sequence of the test and reference loci can vary. In some cases, at least some of the reference loci comprise a common nucleotide sequence. The common nucleotide sequence can be a simple sequence repeat such as a CA repeat, for example. In other instances, at least some of the reference loci comprise different sequences in which there is not a common sequence. In a related fashion, the test locus and the reference loci can comprise a common nucleotide sequence. Here, too, the common nucleotide sequence can be a simple sequence repeat such as a CA repeat. The test locus and the reference loci can also comprise different sequences and not have a common sequences.

In the present invention, the test locus and the reference loci generally include a simple sequence repeat. The use of such sequences gives the methods of the current invention essentially universal applicability, since simple sequence repeats are ubiquitous throughout eukaryotic genomes. Hence, using a probe which is complementary to a particular simple sequence repeat, essentially any region of the genome can be investigated.

D. Amplification

Amplification procedures begin with the acquisition of sample. In general, a nucleic acid sample is provided. If double stranded, the nucleic acid is first denatured to form single stranded nucleic acid using any of a variety of denaturation techniques which are known in the art, including, for example, physical, chemical, enzymatic or thermal means. Typically, strand separation is achieved using heat denaturation at temperatures ranging from 80° C. to about 105° C. for time periods ranging from about 1 to 10 minutes. For cases in which the nucleic acid is RNA, the sample may first be reverse transcribed to form cDNA which is then denatured.

The resulting denatured nucleic acid strands are incubated with preselected primers, and in some instances a probe, under hybridization conditions, i.e., conditions in which the primers, and probe if present, anneal to their respective complementary portions of the single stranded nucleic acid. Primers are selected so that the primer binding sites to which they anneal are located so as to result in the formation of an extension product which, once separated from its template strand, can itself serve as a template for extension by the other primer.

Because the denatured nucleic acid strands are typically considerably longer than the primers and probe (if utilized), there is an increased probability that a denatured strand makes contact and reanneals with its complementary strand before the primer or probe has a chance to hybridize to their complementary sequences. To avoid this problem, a high molar excess of primer and probe (if utilized) are used to increase the likelihood that they anneal to their respective template strand before the denatured strands reanneal. Details regarding the selection and composition of primers is described below.

E. Amplification Options

In general a test or reference locus is amplified using PCR amplification methods (see, for example, PCR Protocols, (Innis et al., Eds.), Academic Press, New York, 1989; Sambrook et al., Molecular Cloning, 2nd edition, Cold Spring Harbor Laboratory, New York, 1989; and U.S. Pat. Nos. 4,683,202, 4,683,195, and 4,965,188). As is typical of amplification methods, two primers (a primer pair) are used to amplify the nucleic acid sequence of interest. In the methods of the present invention, a probe can be used to monitor the formation of amplified products. However, as described in more detail below, the probe is not required and the amplification products themselves can be directly monitored. In those instances in which a probe is used, the probe hybridizes to a nucleic acid segment located between the PCR primers used to amplify the test or reference locus.

The methods of the present invention are also amenable to other amplifications techniques, including, for example, methods broadly classified as thermal cycling amplification methods and isothermal amplification methods. Suitable thermal cycling methods include, for example, ligase chain reaction (Wu and Wallace, Genomics 4:560, (1989); and Landergren et al., Science 241: 1077 (1988)). Isothermal amplification methods useful in the present invention include, for example, Strand Displacement Amplification (SDA) (Walker et al, Proc. Nat. Acad. Sci. USA 89:392–396 (1992)), Q-beta-replicase (Lizardi et al., Bio/Technology 6:1197–1202 (1988)); nucleic acid-based Sequence Amplification (NASBA) (Sooknanan, R., et al., Bio/Technology 13:563–565 (1995)); and Self-Sustained Sequence Replication (Guatelli, et al., Proc. Nat. Acad. Sci. USA 87:1874–1878 (1990)).

F. 5' Fluorogenic Nuclease Assays

Fluorogenic nuclease assays are one specific example of a real time quantitation method that uses a probe to monitor formation of amplification product and which can be used successfully with the methods of the present invention. The basis for this method of monitoring the formation of amplification product is to measure continuously PCR product accumulation using a dual-labeled fluorogenic oligonucleotide probe—an approach frequently referred to in the literature simply as the "TaqMan method" (12, 15–17). These four references are incorporated herein by reference in their entirety for all purposes.

The probe used in such assays is typically a short (ca. 20–25 bases) oligonucleotide that is labeled with two different fluorescent dyes. The 5' terminus of the probe is attached to a reporter dye and the 3' terminus is attached to a quenching dye, although the dyes could be attached at other locations on the probe as well. The probe is designed to have at least substantial sequence complementarity with the probe binding site. Upstream and downstream PCR primers which bind to flanking regions of the locus are added to the reaction mixture.

When the probe is intact, energy transfer between the two fluorophors occurs and the quencher quenches emission from the reporter. During the extension phase of PCR, the probe is cleaved by the 5' nuclease activity of a nucleic acid polymerase such as Taq polymerase, thereby releasing the reporter from the oligonucleotide-quencher and resulting in an increase of reporter emission intensity which can be measured by an appropriate detector.

One detector which is specifically adapted for measuring fluorescence emissions such as those created during a fluorogenic assay is the ABI 7700 manufactured by Applied Biosystems, Inc. in Foster City, Calif. The ABI 7700 uses fiber optics connected with each well in a 96-well PCR tube arrangement. The instrument includes a laser for exciting the labels and is capable of measuring the fluorescence spectra intensity from each tube with continuous monitoring during PCR amplification. Each tube is reexamined every 8.5 seconds.

Computer software provided with the instrument is capable of recording the fluorescence intensity of reporter and quencher over the course of the amplification. These recorded values can then be used to calculate the increase in normalized reporter emission intensity on a continuous basis. The increase in emission intensity is plotted versus time, i.e., the number of amplification cycles, to produce a continuous measure of amplification. To quantify the locus in each amplification reaction, the amplification plot is examined at a point during the log phase of product accumulation. This is accomplished by assigning a fluorescence threshold intensity above background and determining the point at which each amplification plot crosses the threshold (defined as the threshold cycle number or Ct). Differences in threshold cycle number are used to quantify the relative amount of PCR target contained within each tube. Assuming that each reaction functions at 100% PCR efficiency, a difference of one Ct represents a two-fold difference in the amount of starting template.

Additional details regarding the theory and operation of fluorogenic methods for making real time determinations of the concentration of amplification products can be found in references (12, 15–17) and U.S. Pat. Nos. 5,863,736, 5,210,015, 5,538,848. These references are incorporated herein in their entirety for all purposes.

An alternative method for measuring changes in fluorescence occasioned by digestion of a fluorescently labeled probe is the fluorescence polarization method detection system described in U.S. Pat. No. 5,593,867 to Walker et al. (incorporated by reference in its entirety for all purposes). This technique is able to distinguish between large and small molecules based on molecular tumbling. Large molecules (e.g., intact labeled probe) tumble in solution much more slowly than small molecules. Using a probe attached to a fluorescent dye it is possible to measure and differentiate between intact probe and digested probe and thus indirectly obtain a measure of the amount of amplification product formed.

III. Calculations

A. General Approach

As described above in section II, the methods of the present invention utilize four values in order to obtain the copy number of a test locus in a test sample. In certain methods, the four values are measures of the extent of amplification necessary for amplification product to reach a threshold value for the test locus and reference loci in a test subject and a control subject.

As indicated in the section on fluorogenic nuclease assay methods, one measure of the amount of amplification necessary to reach a threshold value is to determine the number of amplification cycles required to reach the threshold value. This value is called a threshold cycle number or simply Ct. Thus, in methods in which Ct values are determined, certain methods of the present invention typically require the determination of four Ct values:

1) a Ct value for the test locus in the test subject (Ct(test marker)),
2) a Ct value for the reference loci in the test subject (Ct(test pooled reference)),
3) a Ct value for the test locus in the control subject (Ct(calibrator test marker)), and
4) a Ct value for the reference loci in the control subject (Ct(calibrator pooled reference)).

Use of Ct values as a measure of amplification is one useful measure of the quantity of the original nucleic acid sequence being amplified, because the software that comes with the ABI 7700 fluorescence instrument manufactured by Applied Biosystems, Inc. automatically makes such calculations. However, it should be understood that other approaches for measuring the rate of formation of amplification product or the time necessary to form a certain level of amplification product can also be used. For instance, instead of calculating the number of amplification cycles necessary to reach a certain threshold value, the increased fluorescence value at a certain time point for each sample can be determined. The fluorescence value can be used in conjunction with a standard curve to determine the amount of amplification product present. Thus, although the equations set forth below are in terms of Ct values, the same mathematical treatment can be used to calculate copy number with any value for the rate of amplification product formation or the time required to form a certain level of amplification product.

Although the ABI 7700 instrument is typically used to monitor fluorescence, the Ct values need not be determined from fluorescence measurements. As noted below, Ct values could be determined from measurements of a variety of different types of signals.

In general the threshold value must be high enough to be statistically different from the baseline value but below the signal obtained for the saturation phenomenon associated with amplification reactions, wherein the baseline value is the magnitude of the signal detected prior to the formation of amplification products. Typically, the threshold value is set at about ten standard deviations above the mean baseline emission value. (See, for example, Heid, et al. Genome Research 6:986–994 (1996)).

B. Specifics Regarding Calculation

Typically, a determination for the value of Ct(test marker) is performed in triplicate with a first sample from the test subject; a mean Ct(test marker) value is calculated from the triplicate measurements. Similarly, a value for the reference loci in the test subject (Ct(test pooled reference)) is also determined in triplicate using a second sample and a mean Ct(test pooled reference) value determined. For each test locus, the values for mean Ct(test marker) and mean Ct(test pooled reference) are then used to calculate a difference value, ($\Delta$Ct (test DNA)), according to Equation 1:

$$\Delta Ct(\text{test DNA}) = \text{mean } Ct(\text{test marker}) - \text{mean } Ct(\text{test pooled reference}) \quad (\text{Eq. 1})$$

A similar determination is performed with corresponding values for at least one control subject. More specifically, for each control subject a value is determined for the test locus in the control subject (Ct(calibrator test marker)) and for the reference loci in the control subject (Ct(calibrator pooled reference)). A difference value for each control subject is then calculated according to Equation 2:

$$\Delta Ct(\text{calibrator DNA}) = Ct(\text{calibrator test marker}) - Ct(\text{calibrator pooled ref.}) \quad (\text{Eq. 2})$$

In certain methods, multiple $\Delta$Ct(calibrator DNA) values are determined using samples from multiple control subjects. The number of control subjects sometimes is at least 5, and typically is between 5 and 10. When multiple control subjects are used, a mean calibrator value is obtained, i.e., mean $\Delta$Ct(calibrator DNA). The $\Delta$Ct(calibrator DNA) or mean $\Delta$Ct(calibrator DNA) serves as a "calibrator" to which ΔCt(test DNA) can be compared. The measure of mean ΔCt(calibrator DNA) and variance about that mean allows for precise determination of whether a measured ΔCt(test DNA) value lies outside the distribution of control (calibrator) ΔCt values.

Unlike other methods, it is not necessary to determine or know the concentration of nucleic acid in the sample or samples used to determine values for the test locus and the reference loci in the test subject (i.e., Ct(test marker) and Ct(test pooled reference)); instead, it is only necessary that amount of nucleic acid used in the test locus and reference loci determinations for the test subject be as close to the same as experimentally possible. Similarly, it is not necessary to determine or know the concentration of nucleic acid in the sample or samples used to determine values for the test locus and reference loci in the control subject (i.e., Ct(calibrator test marker) and Ct(calibrator pooled ref.)); it is only necessary that the amount of nucleic acid used to determine the values for test and reference loci in the control subject be as close to the same as experimentally possible. Finally, it is also not necessary that the amount of nucleic acid used in determining values for the test subject be the same as the amount used in determining values for the control subjects. As described in more detail in Example I, reaction mixtures contain all the components necessary for amplification except the primers for the locus/loci being amplified.

It is not necessary to determine the values for the control subjects at the same time that measurements are made for test subjects. The values for the control subject can be historical. Thus, for example, it is possible to determine copy number values for test subjects using values for the test locus and the reference loci in the control subject which were determined days earlier. In such cases, the methods of the present invention simply involve amplification steps to determine the necessary values for the test locus and the reference loci in the test subject. These values can then be used with the previously determined values for the test locus and reference loci in the control subjects to calculate copy number for the test locus in the test individual.

Regardless of when the ΔCt (calibrator DNA) value is calculated, a difference value, ΔΔCt, is determined which compares the ΔCt (test DNA) value against the mean ΔCt (calibrator DNA) value (the "calibrator") using the equation which follows:

$$\Delta\Delta Ct = \Delta Ct \text{ (test DNA)} - \text{mean } \Delta Ct \text{ (calibrator DNA)} \quad \text{(Eq. 3)}$$

Using the value for ΔΔCt, the relative copy number in a diploid genome can be calculated using the following formula:

$$\text{Relative copy number in diploid genome} = 2(1+E)^{-\Delta\Delta Ct} \quad \text{(Eq. 4)}$$

where E is the PCR efficiency calculated according to the following formula:

$$E = 10^{(1/-S)} - 1 \quad \text{(Eq. 5)}$$

where S equals the slope of a standard curve of a serial dilution of template, when Ct is plotted versus log DNA concentration. The relative copy number is multiplied by 2 to normalize for two copies per cell in a diploid genome.

For simplicity when calculating copy number alterations, PCR efficiencies are assumed to be 100% so that relative copy number alterations are calculated according to the equation:

$$\text{Relative copy number in diploid genome} = 2 \times 2^{-\Delta\Delta Ct} \quad \text{(Eq. 6)}$$

When using this simplification for DNA copy number calculations, it is important that each primer set displays PCR efficiency close to 100%. Generally, a primer set is not used if its efficiency is less than 90%.

The measurement of PCR efficiency is dependent on the slope of the standard curve of a serial dilution of DNA. The curve fit of the line generated to intersect the data points will also be a source of error for this calculation, which is about ±5% in the PCR efficiency measurement. A PCR efficiency measurement is more important for calculating DNA copy number gains than for a single copy loss. This is due to the exponential nature of this measurement. For example, in this calculation a ΔΔCt is large for a large amount of DNA amplification and the assumption that E=1 in the equation for DNA copy number: $2(1+E)^{\Delta\Delta Ct}$, will be affected greater as the ΔΔCt increases. In measurements of DNA losses, the ΔΔCt is always small and hence measurement of losses is less susceptible to the PCR efficiencies different from 1.

C. Statistical Analysis

To determine if a measurement on a single test sample was significantly different from the mean of measurements made on samples from a number of control individuals, a tolerance interval was determined (18). The tolerance interval (TI) was calculated using the mean and standard deviation of ΔCt from each locus or marker and the pooled reference according to the following formula:

$$TI = 2 \times (2^{\pm \{std.\ dev.(all\ markers) \times 2.280^*\}}) \quad \text{(Eq. 7)}$$

*=value generated from a two-sided tolerance limit factor assuming a normal distribution, n=140 (18).

These values represent the range in which a single measured value will 95% of the time fall into this range with 95% confidence.

In equation 7, the value for "std. dev.(all markers)" is a standard deviation determined from the calculated ΔCt (calibrator DNA) values (see equation 2 for calculation) for all the different control subjects at all test loci being interrogated. As an example, assume that five different test loci are being examined and that 10 different control subjects are used as controls. A ΔCt(calibrator DNA) value would be calculated for each of the five loci according to equation 2 for each individual, thus giving 10 ΔCt(calibrator DNA) values for each of the five test loci. For each test locus, a mean and standard deviation value would be calculated from the 10 ΔCt(calibrator DNA) values for that particular test locus, thus giving 5 different means and 5 different standard deviations (a mean and a standard deviation for each test locus). A mean would then be taken of the 5 standard deviations to obtain the value for "std. dev.(all markers)" in equation 7.

The use of a tolerance interval is particularly valuable for analyzing many measurements from a large number of loci and/or specimens. To screen a chromosomal region that may be deleted or amplified in a given tumor, it is more efficient to only measure each locus once and use the tolerance interval to convert that measurement into an integer score. When a number of specimens or loci show similar changes, greater confidence can be gained by repeating the measurement at the most critical loci for each sample and performing a t-statistic. The t-statistic will increase the confidence that any differences in the mean measurements of the specimen are significantly different from the mean measurements of the normal calibrator DNAs, i.e., the mean value for ΔCt (calibrator DNA)

D. Test and Control Reference Pools

In the methods of the present invention, a value is obtained for the quantity of a plurality of reference loci from a test subject. More specifically, in some methods a value is obtained for the extent of amplification required for a plurality of reference loci in nucleic acid from the test subject to reach the threshold value. A similar value is obtained for the control subject(s). This means that a reference value is determined based upon a measurement for multiple loci rather than just a single locus. Experimentally, this means that some methods utilize a reference pool which includes primer pairs for a plurality of reference loci located at different parts of a nucleic acid obtained from a test subject or control subject. When an aliquot of these primers are added to a sample containing nucleic acid from the test subject or control subject, reference loci for which there are complementary primers are simultaneously amplified and a measure of the amount of time (or number of PCR cycles) to reach the threshold value determined. The values obtained using the reference pools (Ct(test pooled reference) and Ct(calibrator pooled reference) serve as reference points against which the value for the test locus in the test subject and control subject are measured, respectively.

One of the concerns in measuring relative DNA copy number is the potential for a reference locus to be altered in copy number (especially in tumors), thus preventing an accurate measurement of a copy number for a test locus. The use of a pooled reference of PCR primers for both test subjects and control subjects helps to reduce the possibility that a chance loss/gain of a reference locus or marker might lead to erroneous assignment of copy number to the test locus. Experience with the methods of the present invention indicate that the loss of a single marker in the pooled reference has only a small influence on the pooled reference and does not alter interpretation of the test loci.

Reference loci to which primers are included in the reference pools are typically selected from regions of the genome that are known on the basis of prior studies to rarely be altered in the tissues under study. Hence, the use of multiplexed loci provides a reference that is representative of the genome and is more stable than individual loci. If a future study were to encounter enough genomic instability that several loci amplified by the primers in the pooled reference might be altered in copy number, there is no a priori reason that the number of primer pairs in the pool could not be increased so as to decrease the impact of any one locus with altered copy number. Typically, the number of primer pairs included in the primer reference pool (and thus the number of reference loci amplified) is at least three. In other instances, such as when there is less certainty regarding the stability of a certain reference locus/loci, at least six primer pairs can be included in the reference pool. In general, the number of reference loci ranges from 6 to 10, although as just indicated, the number can be higher or lower depending upon the particular circumstances.

To determine whether a locus has sufficient stability to be used as a reference locus in the methods of the present invention, a standard deviation is determined for that locus based upon copy number determinations for that locus in multiple control individuals. More specifically, one way for making this determination is to obtain multiple ΔCt (calibrator DNA) values (see equation 2) for multiple control subjects. A standard deviation is then determined from these values. If the standard deviation is above that typically encountered, the locus under investigation is not used as a reference locus. This analysis is performed routinely for all loci, including those which will be combined in the reference pool.

IV. Monitoring Formation of Amplification Product

With the methods of the present invention, it is possible to monitor the formation of amplification products by measuring the amplification products themselves or measuring a detectable signal generated through the alteration of a probe during the extension and amplification process.

A. Non-Probe-Based Detection Methods

A variety of options are available for measuring the amplification products as they are formed. One method utilizes labels, such as dyes, which only bind to double stranded DNA. In this type of approach, amplification product (which is double stranded) binds dye molecules in solution to form a complex. With the appropriate dyes, it is possible to distinguish between dye molecules free in solution and dye molecules bound to amplification product. For example, certain dyes fluoresce only when bound to amplification product. Examples of dyes which can be used in methods of this general type include, but are not limited to, Syber Green™ and Pico Green from Molecular Probes, Inc. of Eugene, Oreg., ethidium bromide, propidium iodide, chromomycin, acridine orange, Hoechst 33258, Toto-1, Yoyo-1, DAPI (4',6-diamidino-2-phenylindole hydrochloride).

Another real time detection technique measures alteration in energy fluorescence energy transfer between fluorophors conjugated with PCR primers (Nagarenko, I. A., et al. Nucleic Acids Research 25:16–21 (1997)) (incorporated by reference in its entirety for all purposes).

B. Probe-Based Detection Methods

1. General Description

These detection methods involve some alteration to the structure or conformation of a probe hybridized to the locus between the amplification primer pair. In some instances, the alteration is caused by the template-dependent extension catalyzed by a nucleic acid polymerase during the amplification process. The alteration generates a detectable signal which is an indirect measure of the amount of amplification product formed.

For example, some methods involve the degradation or digestion of the probe during the extension reaction. These methods are a consequence of the 5'-3' nuclease activity associated with some nucleic acid polymerases. Polymerases having this activity cleave mononucleotides or small oligonucleotides from an oligonucleotide probe annealed to its complementary sequence located within the locus.

The 3' end of the upstream primer provides the initial binding site for the nucleic acid polymerase. As the polymerase catalyzes extension of the upstream primer and encounters the bound probe, the nucleic acid polymerase displaces a portion of the 5' end of the probe and through its nuclease activity cleaves mononucleotides or oligonucleotides from the probe.

The upstream primer and the probe can be designed such that they anneal to the complementary strand in close proximity to one another. In fact, the 3' end of the upstream primer and the 5' end of the probe may abut one another. In this situation, extension of the upstream primer is not necessary in order for the nucleic acid polymerase to begin cleaving the probe. In the case in which intervening nucleotides separate the upstream primer and the probe, extension of the primer is necessary before the nucleic acid polymerase encounters the 5' end of the probe. Once contact occurs and polymerization continues, the 5'-3' exonuclease activity of the nucleic acid polymerase begins cleaving mononucleotides or oligonucleotides from the 5' end of the probe. Digestion of the probe continues until the remaining portion of the probe dissociates from the complementary strand.

However, with certain other detection methods, digestion of the probe is not required. Use of so-called "molecular beacons" are illustrative of one such method. With molecular beacons, a change in conformation of the probe as it anneals results in the formation of a detectable signal. A molecular beacon is a probe that includes two sections, one section at the 5' end and the other section at the 3' end. These sections flank the section of the probe which is anneals to the probe binding site within the locus and are complementary to one another. One end section is typically attached to a reporter dye and the other end section is typically attached to a quencher dye.

In solution, the two end sections can hybridize with each other to form a hairpin loop. In this conformation, the reporter and quencher dye are in sufficiently close proximity that fluorescence from the reporter dye is effectively quenched by the quencher dye. Hybridized probe, in contrast, results in a linearized conformation in which the extent of quenching is decreased. Thus, by monitoring emission changes for the two dyes, it is possible to indirectly monitor the formation of amplification product. (See, for example, Piatek, A. S., et al., Nat. Biotechnol. 16:359–63 (1998); Tyagi, S. and Kramer, F. R., Nature Biotechnology 14:303–308 (1996); and Tyagi, S. et al., Nat. Biotechnol. 16:49–53 (1998)) (these references are incorporated by reference in their entirety for all purposes).

2. Probes

The labeled probe is selected so that its sequence is substantially complementary to a segment of the test locus or a reference locus. As indicated above, the nucleic acid site to which the probe binds should be located between the primer binding sites for the upstream and downstream amplification primers.

In some methods, the nucleic acid sequence of the probe is complementary or substantially complementary to a simple sequence repeat. With such probes, it is possible with the appropriate primers to interrogate essentially any region of the genome given the ubiquitous occurrence of simple sequence repeats throughout the genome. For example, certain methods of the present invention are designed to utilize probes wherein the test locus includes a CA repeat. In this particular case, the probe has the sequence 5'(reporter dye)-TGTGTGTGTGTGTGTGTGTGT-(quenching dye)3' (SEQ ID NO:2). As described in more detail below, the reporter and quenching dyes can be selected from a number of different dyes. For example, the reporter dye can be FAM (6-carboxy fluorescein) and the quenching dye can be TAMRA (6-carboxy tetramethyl rhodamine).

For assays utilizing probes to function properly, it is necessary for the probe to anneal to its complementary sequence before the nucleic acid polymerase reaches the segment of the nucleic acid. There are a variety of parameters which can be modified to achieve this. For example, the probe may be designed to be longer than the upstream primer so that probe annealing occurs preferentially at a higher temperature than primer annealing. Secondly, probe may be added in high molar excess relative to primer concentration. The probe concentration, for example, may be 2 to 20 times higher than the primer concentration. Another technique involves using probes and primers with different thermal stabilities. For example, the nucleotide composition of the probe can be chosen to include more G and C nucleotides, thus imparting greater thermal stability to the probe as compared to the primers. The size of the probe can vary, but generally the probe is at least 10 nucleotides long.

Probes (and primers—see below) can be prepared using chemical synthesis or cloning and cleavage of the desired sequences. Examples of synthetic methods include those described by, for example, Ozaki et al., Nucleic Acids Research 20:5205–5214 (1992), Agrawal et al, Nucleic Acids Research, 18:5419–5423 (1990), Narang et al., Methods in Enzymology, 68:90 (1979); Brown et al., Methods in Enzymology 68:109 (1979); Beaucage et al, Tetrahedron Letters 22:1859 (1981). Probes can also be synthesized using a number of commercially available synthesizers, such as those manufactured by Applied Biosystems, Inc. in Foster City, Calif. using synthetic approaches, such as: Beaucage and Iyer, Tetrahedron 48:2223–2311 (1992); U.S. Pat. Nos. 4,458,066, 4,415,732; 4,973,679 to Caruthers et al.; U.S. Pat. No. 4,980,460 to Molko; and U.S. Pat. No. 4,725,677 to Koster et al.

Probes can also be synthesized to include unnatural backbone groups using phosphate analogs such as phosphorothioate, phosphoroamidates and the like, provided that the inclusion of such analogs does not adversely effect the binding efficiency of the probe.

V. Primers

The primers used in the amplification are selected so as to be capable of hybridizing to sequences at flanking regions of the locus being amplified. The primers are chosen to have at least substantial complementarity with the different strands of the nucleic acid being amplified. When a probe is utilized to detect the formation of amplification products, the primers are selected such that they flank the probe, i.e. are located upstream and downstream of the probe.

The primer must have sufficient length so that it is capable of priming the synthesis of extension products in the presence of an agent for polymerization. The length and composition of the primer depends on many parameters, including, for example, the temperature at which the annealing reaction is conducted, proximity of the probe binding site to that of the primer, relative concentrations of the primer and probe and the particular nucleic acid composition of the probe. Typically the primer includes 15–30 nucleotides. However, the length of the primer may be more or less depending on the complexity of the primer binding site and the factors listed above.

Primers can be synthesized according to the methods described above for synthesizing probes.

VI. Labels for Probes and Primers

The labels used for labeling the probes or primers of the current invention and which can provide the signal corresponding to the quantity of amplification product can take a variety of forms. As indicated above with regard to the 5' fluorogenic nuclease method, a fluorescent signal is one signal which can be measured. However, measurements may also be made, for example, by monitoring radioactivity, colorimetry, absorption, magnetic parameters, or enzymatic activity. Thus, labels which can be employed include, but are not limited to, fluorophors, chromophores, radioactive isotopes, electron dense reagents, enzymes, and ligands having specific binding partners (e.g., biotin-avidin).

Monitoring changes in fluorescence is a particularly useful way to monitor the accumulation of amplification products. A number of labels useful for attachment to probes or primers are commercially available including fluorescein and various fluorescein derivatives such as FAM, HEX, TET and JOE (all which are available from Applied Biosystems, Foster City, Calif.); lucifer yellow, and coumarin derivatives.

Some of the more commonly used dyes and those which are particularly readily available include the fluorescein and rhodamine dyes. Methods for linking these particular dyes to oligonucleotides are described by Marshall, Histochemical J. 7:299–303 (1975), Mechnen et al., U.S. Pat. No. 5,188,934, Bergot et al., and PCT publication PCT/US90/05565.

The use of fluorescent dyes that can participate in fluorescence energy transfer processes can be used with good success in the methods of the present invention. Such dye pairs include a donor/reporter dye and an acceptor/quencher dye. There is substantial guidance in the literature regarding reporter and quencher pairs which can effectively be used in quantitative amplification methods, including: Fluorescence Spectroscopy (Pesce et al., Eds.) Marcel Dekker, New York, (1971); White et al., Fluorescence Analysis: A Practical Approach, Marcel Dekker, New York, (1970); Berlman, Handbook of Fluorescence Spectra of Aromatic Molecules, 2nd Ed., Academic Press, New York, (1971); Griffiths, Colour and Constitution of Organic Molecules, Academic Press, New York, (1976); Indicators (Bishop, Ed.). Pergamon Press, Oxford, 19723; Haugland, Handbook of Fluorescent Probes and Research Chemicals, Molecular Probes, Eugene (1992).

Exemplary reporter and quencher dyes include, but are not limited to, the xanthene dyes, such as fluorescein dyes, and rhodamine dyes. A variety of derivatives of these dyes are commercially available. Often functional groups are introduced into the phenyl group of these dyes to serve as a linkage site to an oligonucleotide. Another general group of dyes includes the naphthylamines which have an amino group in the alpha or beta position. Dyes of this general type include 1-dimethylaminonaphthyl-5-sulfonate, 1-anilino-8-naphthalende sulfonate and 2-p-touidinyl-6-naphthalene sulfoneate. Other dyes include 3-phenyl-7-isocyanatocoumarin, acridines, such as 9-isothiocyanatoacridine and acridine orange, pyrenes, bensoxadiazoles and stilbenes. Additional dyes include 6-carboxy fluorescein, 2',4',5',7',-tetrachloro-4,7-dichlorofluorescein, 2',7'-dimethoxy-4',5'-6-carboxyrhodamine (JOE), N',N',N',N'-tetramethyl-6-carboxyrhodamine (TAMRA), and 6-carboxy-X-rhodamine (ROX). A universal quencher includes (4-dimethylamine) azobenzene sulfonic acid (DABSYL).

Derivatives of reporter and quencher dyes which contain appropriate functional groups for linking the dyes to an oligonucleotide can be synthesized, for example, according to the methods described by Ullman et al. in U.S. Pat No. 3,996,345 and Khanna et al. in U.S. Pat. No. 4,351,760. References directed towards methods of linking reporter or quenching dyes to the 5' or 3' terminus of an oligonucleotide include:

Oligonucleotides and Analogues: A Practical Approach (Eckstein, Ed.) IRL Press, Oxford (1991); Sharma et al., Nucleic Acids Research, 19:3019 (1991) (method for linking to 3' sulfhydryl); Suckerman et al., Nucleic Acids Research 15:5305–5321 (1987) (linkage through 3' thiol on oligonucleotide); and Giusti et al, PCR Methods and Applications, 2:223–227 (1993); Fung et al., U.S. Pat. No. 4,757,141 (5' phosphoamino group introduced through AminoLink™, available from Applied Biosystems, Foster City, Calif.); Nelson et al., Nucleic Acids Research 17:7187–7194 (1989) (linkage through 3' amino group); Sproat et al., Nucleic Acids Research, 15:4837 (1987) (connection through 5' mercapto group); and Stabinsky, U.S. Pat. No. 4,739,044 (linkage via 3' aminoalkylphosphoryl group).

Labels may be attached to the probe or primer using a variety of techniques and can be attached at the 5' end, and/or the 3' end and/or at an internal nucleotide. The label can also be attached to spacer arms of various sizes which are attached to the probe or primer. These spacer arms are useful for obtaining a desired distance between multiple labels attached to the probe or primer.

With commercially available phosphoroamidite reagents, it is possible to synthesize oligonucleotides which contain functional groups such as thiols or primary amines at either the 5' or 3' end using an appropriately protected phosphoroamidite. The functional groups can then be labeled according to various protocols, such as those described in the reference entitled PCR Protocols: A Guide to Methods and Applications (Innis, et al., Eds.) Academic Press, Inc. (1990). Related methods for introducing functional groups into an oligonucleotide are described in U.S. Pat. No. 4,914,210.

In some instances, a single label may be utilized; whereas, in other instances, such as with the 5' fluorogenic nuclease assays for example, two or more labels are attached to the probe. In cases wherein the probe includes multiple labels, it is generally advisable to maintain spacing between the labels which is sufficient to permit separation of the labels during digestion of the probe through the 5'-3' nuclease activity of the nucleic acid polymerase.

VII. Applicability

The methods of the present invention provide a rapid, accurate and inexpensive way to determine copy number. This makes the methods ideal for the molecular analyses of numerous diseases, as well as assessment of chromosomal imbalances associated with health threatening syndromes.

A. Development of Molecular Pathology Profiles

Many chromosomal regions or specific genes have been identified as being present at altered copy number in cancer cells. The copy number for any particular locus is typically 2 in a diploid individual, reflecting the presence of one copy of a locus on each chromosome. It is widely accepted that copy number changes cause abnormal levels, or activity, of proteins encoded by these regions and ultimately the eventual tumor phenotype. Currently, however, physicians tend to rely primarily simply on tumor pathology in choosing between treatment options. Such reliance is problematic because tumors with similar pathology often respond differently to the same treatment.

With the methods of the present invention, however, copy number changes can be enumerated at essentially any region in the genome. Furthermore, with the methods of the present invention screens can rapidly and inexpensively be performed. Hence, the methods of the present invention are well-suited to development of molecular pathology profiles which allow physicians to make more informed patient prognoses and to better predict patient response to different therapies, thus improving clinical outcomes.

1. Diagnostic Information

Use of the methods of the present invention to acquire diagnostic information involves obtaining a sample from a number of different individuals known to have a common disease and conducting screening tests to determine copy number at a number of different test loci for each of the diseased individuals to identify those loci having altered copy number (i.e., a copy number value different than 2). For example, for individuals having a skin tumor, a sample would be taken from the tumorous region of the skin for each individual and screens performed to identify regions of the genome having altered copy number. With such information, correlations between loci having altered copy number and particular diseases can be made. Hence, the methods of the present can be used to identify the alteration of loci which are associated with specific diseases.

2. Prognostic Information

In a related fashion, the methods of the present invention can be used to develop correlations between certain disease phenotypes and patient prognosis. For example, the methods of the present invention can be used to screen numerous loci from a variety of different patients having the same apparent disease symptoms to identify those loci which have an abnormal copy number. In this instance, samples would be obtained from the diseased tissue. A health history for each test individual can be maintained to make a correlation between loci having altered copy number and disease outcomes. In this way, correlations between copy number changes and patient prognosis can be made.

3. Identification of Optimal Treatment Strategies

The methods of the present invention can also be used to identify which treatment option is best suited for a particular disease. Using the screening methods just described, individuals having the same phenotype and similar copy number alterations can be identified. Once a group of such individuals are identified, the group can be broken up into different groups, each group being treated according to a different treatment protocol. By tracking the health status and response of the patients to the various treatment options, correlations between specific copy number alterations and the effectiveness of various treatment protocols can be made.

B. Use of Current Methods as Screening and Therapeutic Tool

In instances in which certain copy number alterations have already been correlated with disease, then the methods of the present invention can be utilized as a diagnostic tool, a prognostic tool and as a means for assessing the success of various treatment options.

1. Patients Exhibiting Symptoms of Disease

For patients having symptoms of a disease, the methods of the present invention can be used to determine if the patient has copy number alterations which are known to be linked with diseases that are associated with the symptoms the patient has. For example, for a patient having a tumor, a physician would obtain a sample of the tumor. Screening of the tumor sample to identify whether there is a copy number alteration at loci known to be associated with the particular tumor type can rapidly be accomplished using the methods of the present invention. With specific information regarding copy number alterations and knowledge of correlations between disease outcomes and the effectiveness of different treatment strategies for the particular alteration(s), the physician can make an informed decision regarding patient prognosis and the most effective treatment option.

For example, if the methods of the present invention show that a particular locus is amplified and that amplification of that locus is associated with poor recovery, the physician can counsel the client regarding the likely effectiveness of aggressive treatment options and the option of simply foregoing such treatments, especially if the disease is quite advanced. On the other hand, if the copy number is altered at a locus which is associated with good recovery, the physician can describe a range of treatment options varying from simply monitoring the disease to see if the condition worsens or more aggressive measures to ensure that the disease is attacked before it gets worse.

2. Patients that are Susceptible to a Disease

The methods of the present invention are also particularly valuable for screening individuals that know they are susceptible to a disease. In this scenario, for example, the individual would know from family history or previous test results showing the presence of a disease marker that he or she was susceptible to disease. In this instance, a sample would be removed from the tissue which the disease to which a patient is susceptible is typically associated. Thus, for example, if the patient comes from a family with a history of breast cancer, a physician would perform a biopsy of the breast to obtain the sample. A copy number value of the locus or loci associated with the particular disease to which the patient is susceptible can then be determined using the methods of the present invention. If the determination shows an abnormal copy number (i.e., a copy number other than 2), the patient can then be counseled regarding the likelihood that the patient will begin suffering from disease and the pros and cons regarding different treatment alternatives. In this instance in which the patient is not yet exhibiting symptoms of disease, the most appropriate action may be simply to closely monitor the patient. However, the patient, after appropriate counseling, may chose to take aggressive preemptive action to avoid problems at a later date.

3. Patients Having No Symptoms of Disease and not Known to be Susceptible to Disease The methods of the present invention can also be useful in screening individuals which have no symptoms of disease or no known susceptibilities to disease. An individual in this category would generally have no disease symptoms, have no family history of disease and have no knowledge that he or she carried a marker associated with a disease. In such cases, the methods of the present invention can be used as a useful preventive screening tool. Using the methods of the present invention, a number of selected loci known to be associated with certain diseases can be interrogated to identify loci with aberrant copy number. In this case, samples would be obtained from the different tissues or fluids that are affected by the disease(s) being tested for. If a locus or loci were identified that had an altered copy number, then the patient would be advised regarding the likelihood that the disease would manifest itself and the range of treatment options available.

4. Examples of Diseases that can be Monitored

A number of cancers are associated with changes in the copy number of certain a certain locus. For example, the methods of the present invention can be used with essentially any number of different oncological markers, including, but not limited to, those listed in Table I below.

TABLE I

Potential Oncological Markers for DNA Copy Number Analysis

| Gene | Cytogenetic localization |
| --- | --- |
| p58clk-1 | 1p36 |
| N-myc | 2p23–24 |
| EGR-1 | 5q31 |
| CSF1R | 5q33.3–34 |
| Estrogen Receptor | 6q25.1 |
| c-myc | 8q24 |
| abl | 9q34 |
| INT-2 | 11q13.3 |
| HST | 11q13.3 |
| Cyclin D1 | 11q13 |
| MLL | 11q23 |
| GLI | 12q13 |
| Retinoblastoma | 13q14 |
| CLL | 13q14 |
| p53 | 17p13.1 |
| HER2/neu(ERBB2) | 17q11.2–q12 |
| Breast cancer amplicon | 20q13 |
| bcr | 22q11 |
| Andogen Receptor | Xq12 |

Similarly, the methods of the present invention can also be used to detect the duplications and deletions associated with certain duplication and deletion syndromes, including, but not limited to, the diseases listed in Table II below:

TABLE II

Duplication and Deletion Syndromes

| Disease | Chromosomal region and changes |
| --- | --- |
| Wolf-Hirschorn | −4p |
| cri du chat | −5p |
| Williams* | −7q11.23 |
| Trisomy 8 | +8 |
| Duplication 9 | +9p |
| Prader-Willi/Angelman | −15q11–13 |
| Miller-Dieker* | −17p13.3 |
| DiGeorge/velocardiofacial/Shprintzen | −22q11 |

* = Very difficult to see with existing methods

5. Prenatal Diagnostics

Another major use of the methods provided by the current invention is in the area of prenatal diagnostics, in particular, as a way to identify DNA copy number abnormalities in a fetus. An increasingly common trend is for women to wait until later in life to have children. Associated with this delay, is an increased risk that the child will be born with a congenital birth defect.

To test for the presence of copy number alterations associated with certain birth defects, a sample can be obtained from the fetus. However, the methods of the present invention can also be used with fetal cell sorting procedures. Hence, the methods described herein provide a less invasive and less expensive way to conduct testing as compared to amniocentesis and chorionic villus sampling. The methods of the present invention can also be used to detect microdeletions that other methods are unable to detect.

VIII. Sample Types

The samples used in the present methods can come from essentially any organism. In methods utilizing probes specific for simple sequence repeats, the samples can be obtained from essentially any eukaryotic organism, including, but not limited to, humans, mice, rats, hamsters, horses and cows.

The sample can be derived from essentially any source associated with an organism such as a sample of tissue or a fluid obtained from an individual or a group of individuals. Illustrative examples include skin, plasma, serum, blood, urine, tears, organs, spinal fluid, lymph fluid and tumors. The sample can also be derived from in vitro cell cultures, including the growth medium, recombinant cells and cell components.

When samples are taken for diagnosis or study of a tumor, the sample typically is taken from tumor tissue or tissue suspected to have the beginnings of tumor formation. With enrichment techniques, the necessary sample for assessment of tumor presence can be obtained by enriching tumor cells or DNA from plasma, for example.

The following examples are provided to further illustrate specific aspects of the invention but are not to be construed so as to limit the scope of the present invention.

EXAMPLE I

Materials and Methods

A. Specimens

The methods of the present invention were used to quantify loci in inbred strains of mice using two model systems. One model system was an FVB knock out mouse (designated M11) that lacked 700 kb of chromosome 11 (kindly provided by Dr. E. Rubin, Lawrence Berkeley National Laboratory, Berkeley, Calif.). Tail DNA samples were obtained from M11 +/+, +/− and −/− FVB mice. In the second system, simple sequence repeat analyses of chromosome 2 loci in radiation-induced leukemias in an inbred mouse strain were performed to evaluate tumor-associated allele loss. At 3 months of age, SJL mice (Jackson Laboratories, Bar Harbor, Me.) were exposed to 3 Gy ionizing radiation from a cesium irradiator. After 7–9 months, spleen and marrow were harvested for DNA isolation.

Human DNA included blood and tumor samples. Blood was collected from normal, healthy male and female donors. A human prostate tumor sample was obtained from the tissue bank of the UCSF Moffitt Hospital. This tumor specimen, obtained during radical prostatectomy, had been fixed in formalin and embedded in paraffin for conventional histological examination. Fifty sections (5 microns in thickness) were obtained from a region identified microscopically to contain primarily tumor tissue. All specimens were collected and utilized with approval from the Committee on Human Research at the University of California, San Francisco.

Five breast cancer cell lines with previously characterized amplifications on chromosome 20q (13) were used to quantify amplified regions using the methods of the present invention. HBL100, MDA MB361, HS578T, SKBR3 and MCF-7 breast cancer cells were obtained from the American Type Tissue Culture Collection (Rockville, Md.) and cultured as recommended by the supplier.

B. DNA Preparations

DNA was extracted from either tail clippings or spleens of mice and processed with a Puregene DNA extraction kit (Gentra systems Minneapolis, Minn.) used according to the manufacturer purification recommendations.

DNA was extracted from human blood specimens and cell lines using a Wizard™ Genomic DNA purification kit from Promega (Madison, Wis.). BAC (bacterial artificial chromosome) DNA extractions were conducted using a Qiagen column according to manufacturer recommendations (Qiagen, Santa Clarita, Calif.).

DNA was extracted from the paraffin-embedded human prostate tumor sections using phenol: chloroform: isoamyl alcohol (PCI). Briefly, paraffin was removed by incubating with Americlear (Baxter, Inc. Deerfield, Ill.) at 37° C. for 20 minutes. After centrifugation and supernatant removal, the pellet was dehydrated by resuspension in 100% ethanol twice followed by air drying. The precipitate was then resuspended in 2 ml digestion buffer (0.5% SDS in 10 mM NaCl, 25 mM EDTA, 10 mM Tris pH 8.0) with 0.3–0.5 mg/ml proteinase K (Sigma, St. Louis, Mo.) and incubated at 55° C. overnight. On subsequent days an equal amount of fresh proteinase K was added for repeated overnight incubations until tissue particles were no longer visible. This usually required 3 to 5 days of proteinase K treatment. DNA was then extracted using PCI, precipitated in ethanol and redissolved in TE buffer (10 mM Tris, 1 mM EDTA, pH 7.5).

C. Oligonucleotides

PCR primer sequences for simple sequence repeat loci were obtained from the Whitehead Institute MIT Center for Genome Research using either of two databases; (i.) Genetic and Physical Maps of the Mouse Genome, or (ii.) Human Physical Mapping Project. Primers were synthesized by Gibco, Life Sciences, Gaithersburg, Md. The reference pool contained primer pairs for six or seven different simple sequence repeat loci located at different sites in the genome. For human DNA analyses seven sites were chosen that usually did not show alterations when human prostate or breast tumors were analyzed by CGH (14). The simple sequence repeat markers used were, D4s1605, D5s478, D11s913, D12s1699, D14s988, D21s1904 and D22s922. For mouse analyses, reference pool loci were chosen from random sites around the genome. These were, D1Mit64, D2Mit175, D3Mit12, D12Mit10, D13Mit250, and D14Mit5.

The TaqMan™ CA-repeat fluorogenic probe consisted of the following sequence: -5' FAM (6-carboxy fluorescein)-TGTGTGTGTGTGTGTGTGTGT-TAMRA (6-carboxy tetramethyl rhodamine) 3' (SEQ ID NO:1). ZNF217 primers and probe were as previously reported (13). Both probes were purchased from Perkin Elmer, Foster City, Calif.

D. Quantitative PCR Analysis

In the examples which follow, 5' fluorogenic nuclease assays were utilized to perform real time quantitative PCR. Details regarding this method are described above in section II(F) and in references (12, 15–17). The assays were used to determine the relative abundance of each CA repeat within a test or reference locus. However, it should be appreciated that the methods of the present invention do not require the use of simple sequence repeats. Furthermore, the methods of the present invention can also utilize real time amplification methods other than the fluorogenic nuclease assays such as the TaqMan method.

For each locus, PCR was conducted in triplicate with 50 μl reaction volumes of 1×PCR buffer A (Perkin Elmer, Foster City, Calif.), 2.5 mM $MgCl_2$, 0.4 μM each primer, 200 μM each dNTP, 100 nM probe and 0.025 u/μl Taq Gold (Perkin Elmer, Foster City, Calif.). For each experiment, a master mix of the above components was made and aliquoted into each optical reaction tube. Each primer set (5 to 10 μl volume for reproducibility) was then added, and PCR was conducted using the following cycle parameters: 95° C. 12 min×1 cycle, (95° C. 20 sec, 55° C. 20 sec, 72° C. 45 sec)×40 cycles.

As described above, analysis was carried out using the sequence detection software supplied with the ABI 7700. This software calculates the threshold cycle (Ct) for each reaction and Ct values were used to quantitate the amount of starting template in the reaction. The Ct values for each set of three reactions were averaged for all subsequent calculations. Pooled variance for all sets of PCR triplicates was 0.018 (n=288), indicating sufficient statistical power with this level of intra-assay variation to detect a difference of 0.25 cycles between samples with greater than 95% confidence.

EXAMPLE II

Comparative Methods

A. FISH

DNA probes for mouse chromosome 2 were obtained from a BAC library (19) and screened using PCR with primer pairs for D2Mit356 and D2Mit62 as previously described (20). In addition, a BAC clone that was previously selected to contain D2Mit415 was obtained from C. Collins (UCSF). DNA from one BAC clone for each STS was extracted and purified using a midi-prep column according to manufacturer recommendations (Qiagen, Santa Clarita, Calif.), and each DNA was labeled by nick-translation to incorporate fluorescent nucleotides (21). The BAC containing D2Mit356 (BAC356) was labeled with Texas Red, while the other two BACs (BAC62 & BAC415) were labeled with fluorescein. Murine splenic cells were placed on microscope slides and fixed using acetic acid-methanol fixation.

A mixture of the Texas Red-BAC356 with each of the fluoresceinated BACs was hybridized to these samples as described by Pinkel et al. (21). Briefly, cells were denatured in 70% formamide-2×SSC, pH7 at 75° C. for 2–5 min and then slides were dried in a graded ethanol series. The hybridization mixture containing labeled probes (10 ng each) and 1 μg mouse Cot-1 DNA (Gibco, Life Technologies Inc., Gaithersburg, Md.) was heat denatured at 750 C. for 5 min. and reannealed at 37° C. for 60 min. After overnight hybridization at 37° C., slides were washed in 2×SSC and counter stained with 4',6-diamidino-2-phenylindole hydrochloride (DAPI) at 0.01 μg/ml in antifade solution (22). Slides from 5 mice were viewed under a Zeiss Axioplan fluorescence microscope with double-band pass filters (Chroma Technology, Brattleboro, Vt.) and a 63×oil objective. Green (fluorescein labeled segments) and red spots (Texas Red labeled segments) were enumerated in at least 100 metaphase or interphase nuclei for each sample.

B. Comparative Genomic Hybridization (CGH)

CGH was performed on DNA from three SJL mice as described by Kallioniemi et al. (23). Briefly, DNA from spleen cells of an unirradiated SJL mouse was fluorescently labeled by nick-translation and incorporation of nucleotides labeled with Texas Red. Spleen cell DNA from each irradiated mouse was labeled by nick-translation for incorporation of fluoresceinated nucleotides. Mouse metaphase chromosome spreads were prepared from phytohemagglutinin-stimulated murine peripheral blood lymphocytes of a normal C57BL mouse. Both labeled DNAs were co-hybridized to the metaphase spreads in the presence of excess mouse Cot-1 DNA (Gibco, Life Technologies Inc., Gaithersburg, Md.). Image analysis was conducted essentially as described by Piper et al (24).

EXAMPLE III

Copy Number Determination for Human X-chromosome Markers in Males

The single copy of the X-chromosome and two copies of all autosomes in normal male cells provide a simple model system to test the utility of the methods of the present invention. Simple sequence repeat markers were chosen from three different regions of the X-chromosome and from three separate autosomes, 8, 15 and 17. All data was normalized using a pool of primers for 7 different simple sequence repeat loci located at different sites in the genome. This pool provided a reproducible PCR reference reaction to which any individual locus being tested could be compared. Four males and four females were used to measure the DNA copy number on the autosomes and the X chromosome. Assays were conducted as described in Example I.

FIG. 1 shows that this method detects two copies (mean=2.17, Std Dev.=0.07) for the three autosomal markers in male DNA and one copy (mean=0.92, Std Dev.=0.12) for the three X-chromosome markers. The error bars represent the 95% confidence limits based on the variation of measurements for each marker.

This study demonstrates the ability of the methods of the present invention to differentiate between one copy of the X chromosome and two copies of the autosomes in males. More generally, this example demonstrates that the methods are capable of measuring a difference of one or two copies very rapidly.

EXAMPLE IV

DNA Loss in Human Prostate Adenocarcinoma

Quantitative determinations of copy number were performed at four simple sequence repeat loci on DNA isolated from a microdissected, paraffin-embedded prostate adenocarcinoma. This tumor had previously been analyzed by both CGH and LOH and showed a loss of copy number throughout the p arm of chromosome 8.

Figure 2:
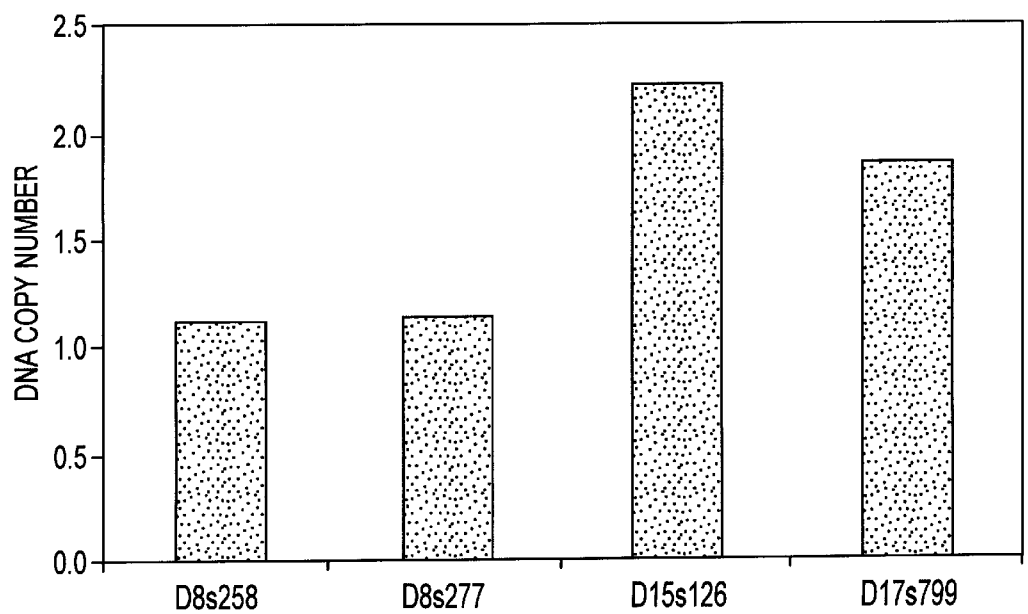
FIG. 2. depicts the relative DNA copy number of markers on the p-arm of chromosome 8 and chromosomes 15 and 17 and the ability of the methods of the present invention to detect DNA loss. Patient DNA was extracted from micro-dissection of tumor tissue embedded in following a radical prostatectomy. Measurement at markers D8s258 and D8s277 indicate that there is only one copy present at these loci compared to two copies at D15s126 and D17s799. This illustrates the possibility of using the methods of the present invention on archival tissues.

Assays were conducted as described in Example I and used the pooled reference as described in Example II. The DNA used in making the determinations of values for the control subjects was a set of DNAs from peripheral blood lymphocytes obtained from ten healthy volunteers. Results for tests conducted using the assay described in Example I indicated a relative DNA copy number of one for markers located on the short arm of chromosome 8 (D8s258 and D8s277) and two for the markers located on chromosomes 15 and 17 (D15s126 and D17s799) (FIG. 2).

Agreement of these results with the LOH and CGH results demonstrates that the methods of the present invention are sensitive enough to resolve a difference of one PCR cycle (=loss of one copy) for DNA isolated from paraffin embedded tissue. Hence, the methods described herein are useful for molecular analysis of archival tissue and do not require a paired normal sample from the patient being tested.

EXAMPLE V

DNA Amplifications in Human Breast Cancer Cell Lines

In previous studies, CGH and FISH have shown DNA copy number increases at the q13 region of chromosome 20 in breast cancer (14, 25). This same region was analyzed using the assay described in Example I on DNA isolated from five different breast tumor cell lines to determine if the method described in Example I was capable of identifying DNA amplifications. The pooled reference and DNA for the control subject were the same as described in Example IV.

Figure 3A:
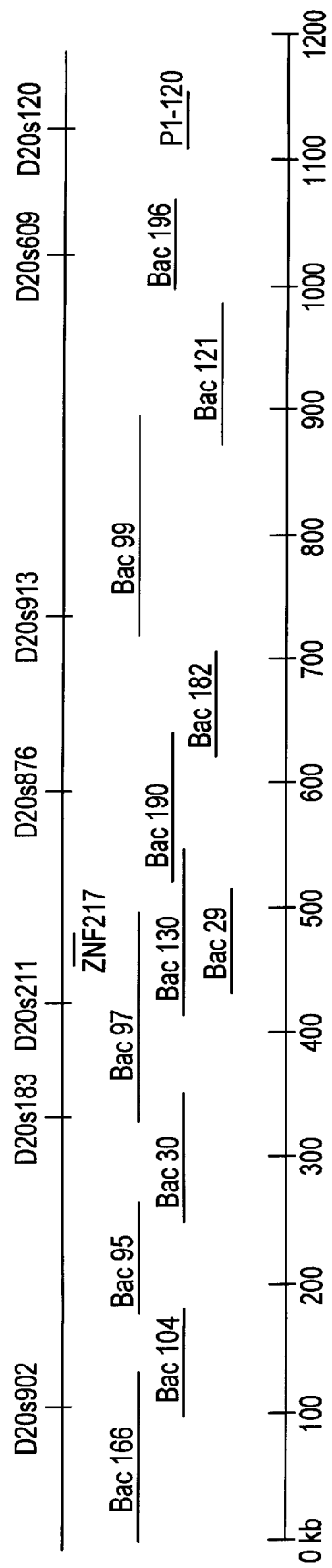
FIGS. 3A–3C show results for DNA amplifications in human breast cancer cell lines using methods of the current invention versus results obtained using FISH.
Figure 3B:
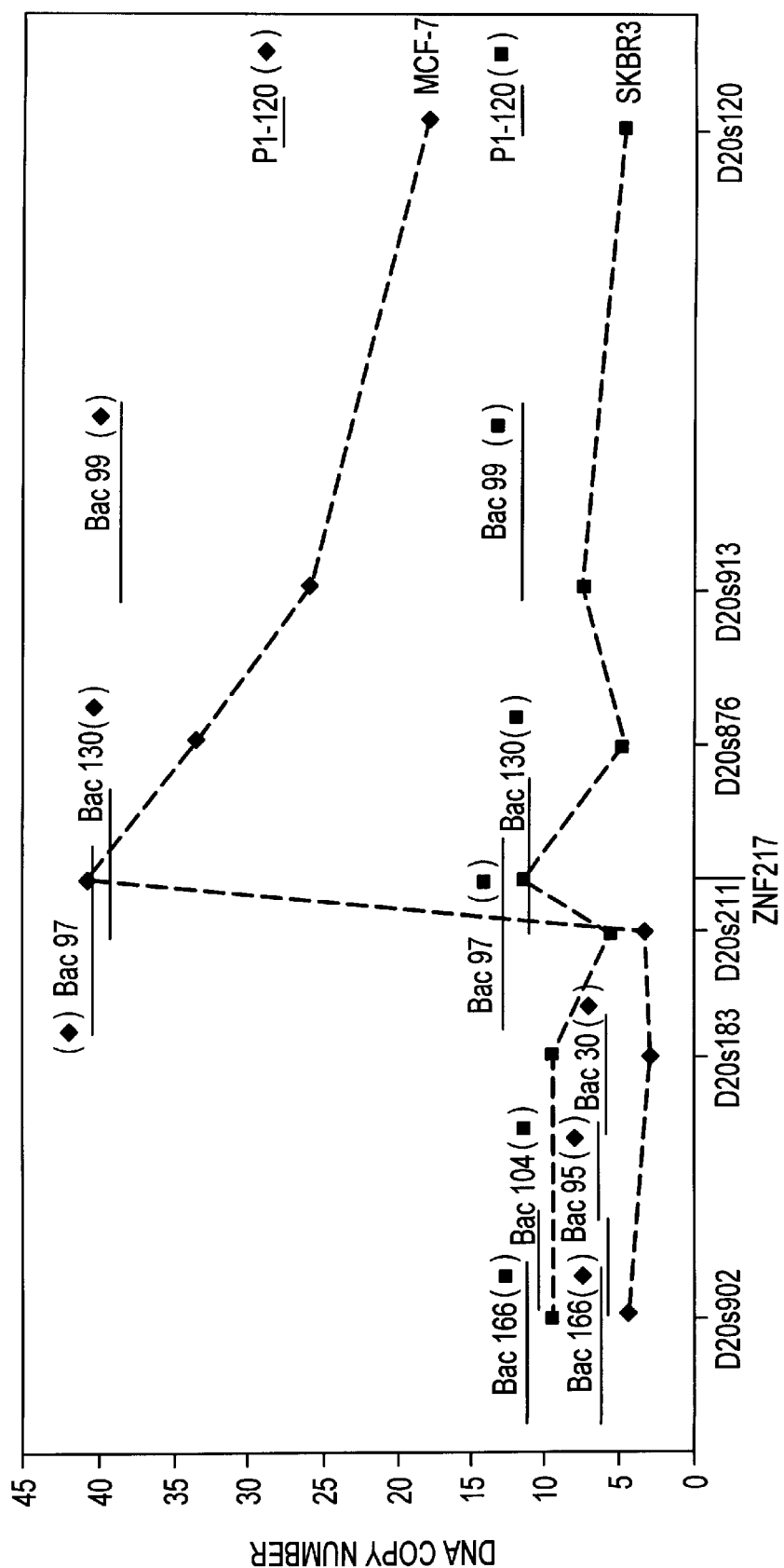
Figure 3C:
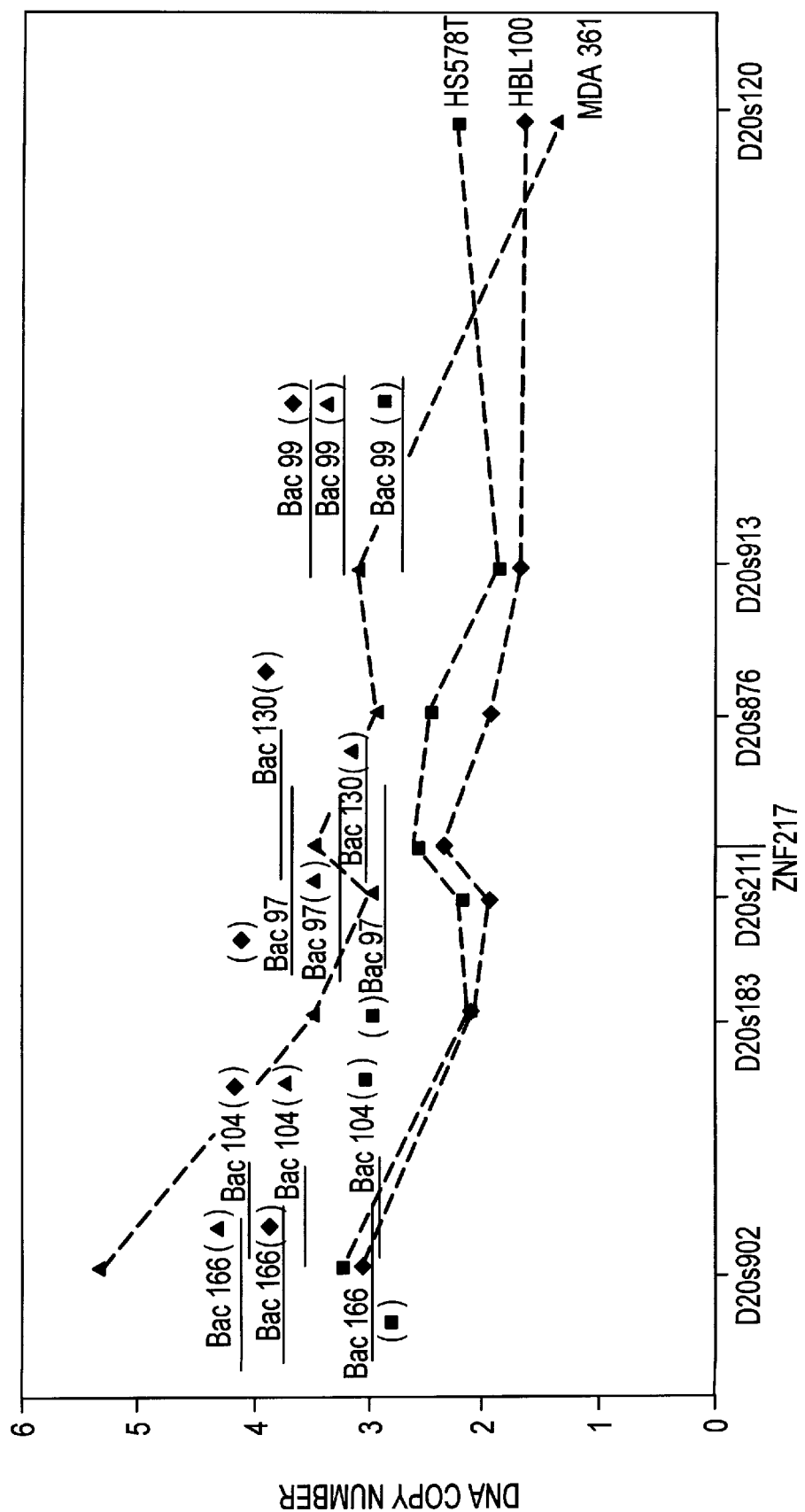

FIGS. 3B and 3C show the data generated by the method described in Example I for the five cell lines (MCF-7, SKBR3, HS578T, HBL100 and MDA 561) and compares the results for these lines with FISH data generated previously (13). These two methods both show that cell lines HBL100, MDA MB 361 and HS578T show only modest increases (less than 5 copies) in DNA copy number at the 20q13 loci. SKBR3 and MCF-7, however show high-level copy number increases with maximal amplification of 12- and 40-fold, respectively, at the ZNF217 locus.

The extent of amplification of 20q13 in the breast cell lines as detected by FISH and the assay described in Example I differ slightly. However, this is not a surprising result, since the two techniques analyze very different sized regions of the genome. This is made evident in FIG. 3A, where the length of each BAC used for FISH is displayed (range 70 to 150 Kb), and the relative size of the regions measured by the methods of the present invention (100 to 150 bp) are also shown. For FISH, if any amplified region contains a significant fraction of the BAC being hybridized, it will result in a large number of hybridization signals even though only part of the BAC sequence is amplified. Thus, precise localization and quantitation of amplification is not possible with large FISH probes such as BACs. The methods of the present invention, however, show amplification of very small, localized regions and thus gives much higher resolution for amplicon mapping. In addition, FISH measurements are made on interphase nuclei and it is often difficult to resolve the exact number of signals from probes in a region of high level amplification.

This study demonstrates that the methods of the present invention can achieve high levels of resolution and determine the degree of copy number amplification more accurately and quickly than is possible with FISH.

EXAMPLE VI

Mouse Model for Deletion Mapping

In this model system a large portion of mouse chromosome 11 was targeted for a homologous recombination experiment, resulting in a 700 kb deletion in this chromosome. This model provided a unique opportunity to further test the methods of the present invention by using hemizygous knock out mice as surrogates for complete loss of one allele, such as might occur in a tumor. A CA-repeat simple sequence repeat locus (D11Mit23) contained in the region of knock out was identified and confirmed by PCR of DNA from a homozygous knock out mouse (data not shown).

Figure 4:
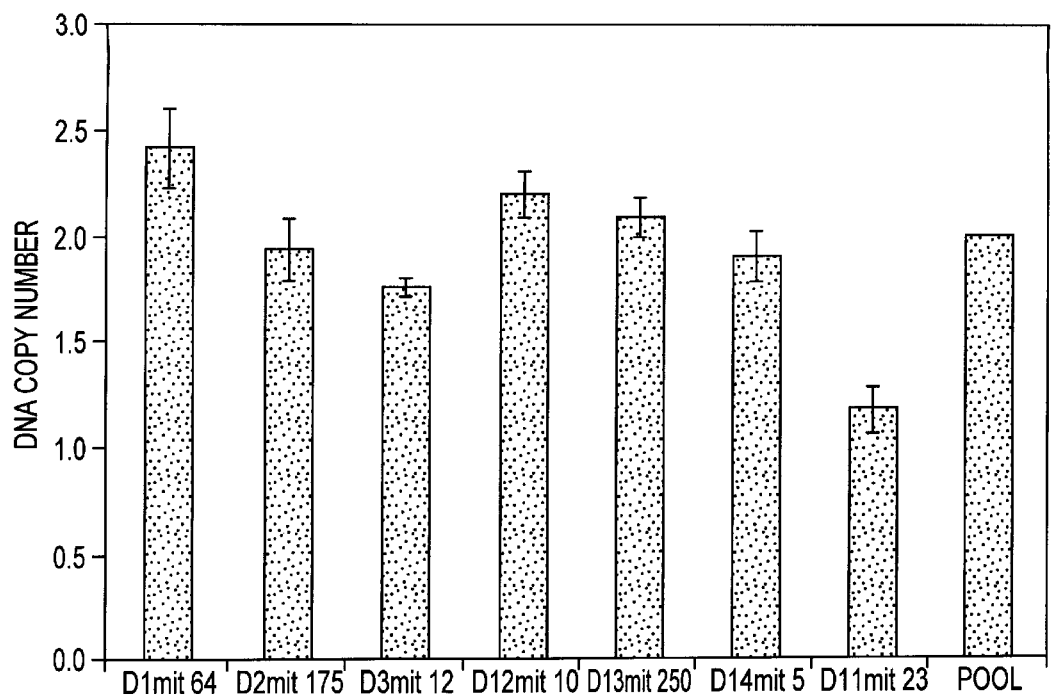
FIG. 4 shows results for relative DNA copy number of 7 markers on various chromosomes and the pooled reference in mice. This is a compilation of 4 experiments for each locus. The DNA used for these experiments is from a hemizygote for a knockout region in chromosome 11. The marker D11Mit23 is located in the region of chromosome 11 that is knocked out in this mouse model. This marker is present at about one copy (1.17) and this value is significantly different from all other loci (p<0.001).

Assays were conducted as described in Example I. Using such assays, D11Mit23 and six other simple sequence repeat markers on mouse chromosomes 1, 2, 3, 12, 13, and 14 were evaluated for DNA copy number in hemizygous knock out mice (FIG. 4). The pooled reference reactions contained primer pairs for all six of the markers outside the knock out region. D11Mit23 was the only locus measured to be present at one copy ($1.17\pm0.11$); all other markers, D1Mit64, D2Mit175, D3Mit12, D12Mit10, D13Mit250, and D14Mit5, were present at two copies (average of six loci= $2.05\pm0.25$). Assays as described in Example I, were repeated for each marker at least four times including one experiment in which the pooled reference contained the deleted marker D11Mit23. This run gave results that were not significantly different from the other three runs (data not shown). Hence, this study illustrates the ability of the methods of the present invention to detect single copy loss, such as in this case, for an organism which is hemizygous for a knockout region of a particular chromosome.

Figure 5:
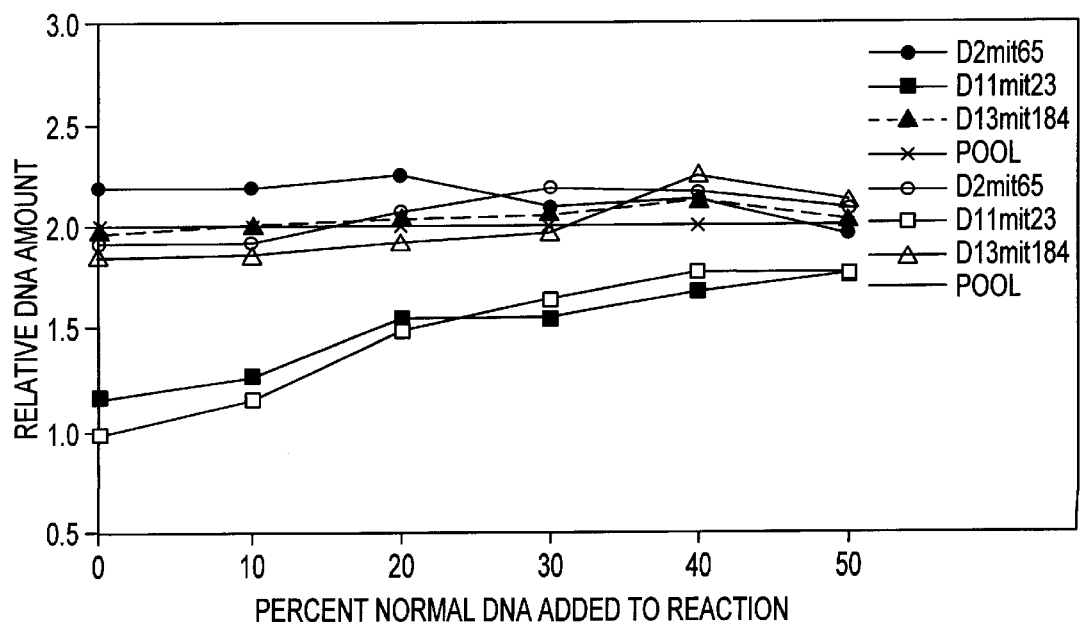
FIG. 5 depicts the results for DNA mixing experiment in which normal SJL mouse DNA was mixed with chromosome 11 knockout hemizygote DNA in increments of 10%. DNA copy number was measured with marker D11MIT23 (□-experiment 1 and ■-experiment 2) and is compared to markers in other chromosomes, namely, D2MIT65 (○-experiment 1 and ●-experiment 2) and D13MIT184 (△-experiment 1 and ▲-experiment 2). These results clearly demonstrate that there is a copy number of about one in the hemizygote DNA sample with marker D11Mit23 (in the knocked out region). Adding normal DNA in 10% increments to the PCR reactions, there is a steady increase of DNA copy number at D11MIT23 up to 50% admixture with normal. With these data there is 80% power (with 95% confidence) to detect a "loss" with 30% normal "contamination."

To further define the limits of the methods of the present invention, a mixing experiment was performed in which aliquots of DNA from the chromosome 11 knock out hemizygote were mixed with different amounts of normal FVB mouse DNA (0–50%). Assays were performed as described in Example I on these DNA mixtures at D11MIT23, D2MIT175 and D13MIT250; results are shown in FIG. 5. Results from such assays on pure knock out mouse DNA gave results indicating that D11Mit23 had one copy while the chromosome 2 and 13 markers were present at 2 copies. As the fraction of normal DNA in the mixture increased, there was a proportional increase in the measured DNA copy number. Even with 30% normal FVB mouse DNA in the reaction mixture, the assays were capable of detecting a difference between one and two copies 90% of the time, with 95% confidence. This result shows that when performing the methods of the present invention on tumor samples, even those contaminated with up to 30% normal cells, the methods can provide sufficient sensitivity to determine loss of one allelic copy at any simple sequence repeat locus of a diploid tumor.

EXAMPLE VII

Identification of Deletions in Leukemias

The SJL mouse strain has previously been shown to be sensitive to radiation-induced leukemia and is often found to have a hemizygous loss of DNA in a 30 cM region encompassing the E-band of chromosome 2 (26, 27). Using the assay method described in Example I, the current inventors also delineated the deletions to 23 cM of the same 30 cM region. Ongoing studies with the methods of the present invention are expected to further refine the minimal region of deletion in this mouse model.

Figure 6:
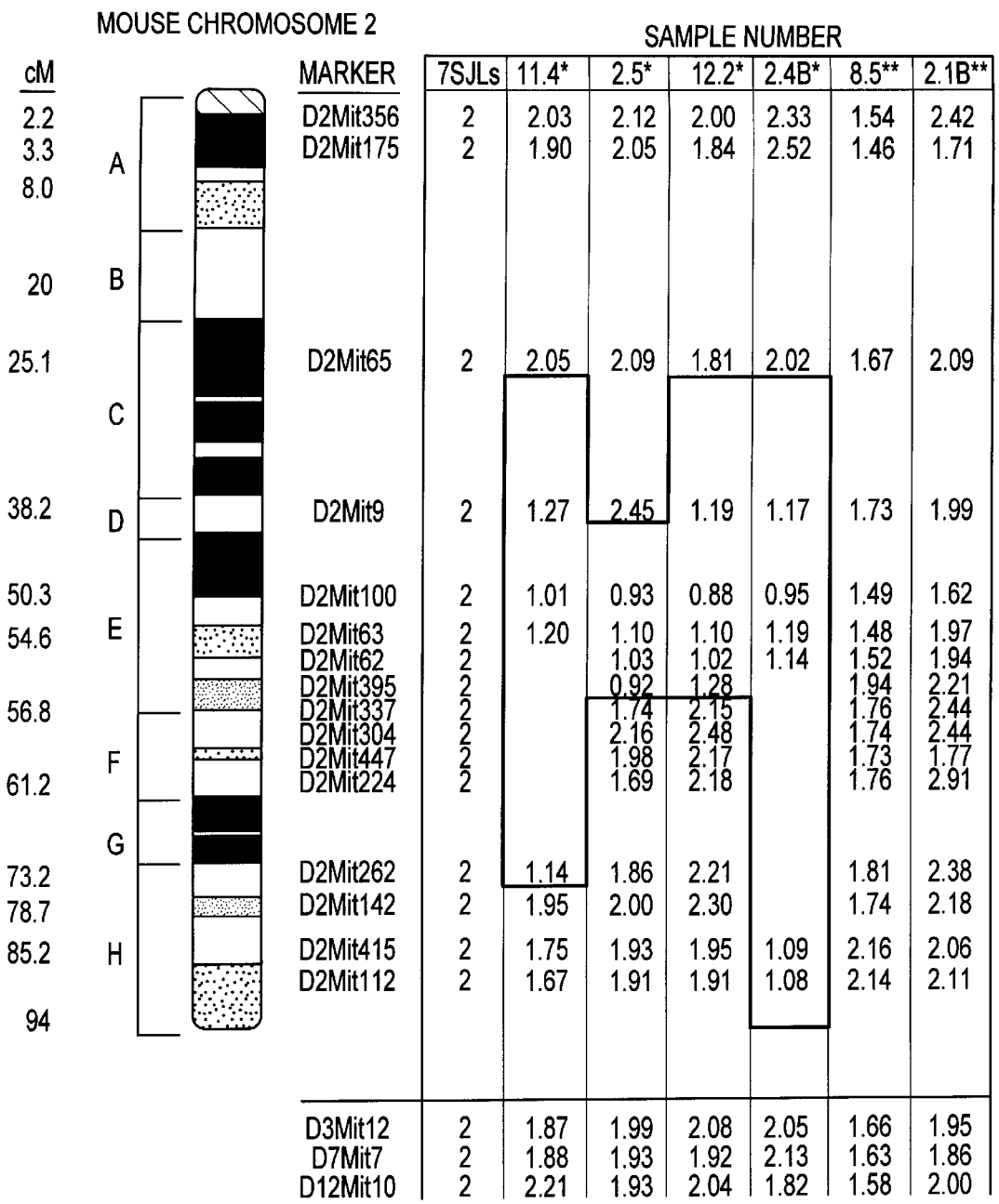
FIG. 6. depicts results from studies with leukemic and normal mice which were measured for DNA copy number using the methods of the current invention at 16 chromosome 2 loci and 3 other chromosomal locations. In the 4 leukemic mice, there is a consistent pattern of deletion of this chromosome. The minimum region of common deletion is between markers D2MIT9 and D2MIT337, a region of about 23 cM. The tolerance interval assumes that the values follow a normal distribution.

Spleen samples were obtained from 8 irradiated SJL mice, 6 of which had developed acute myeloid leukemia. Assays were conducted as described in Example I. Using seven un-irradiated SJL mice to define the normal variation associated with measurements obtained using such assays at each locus tested, a tolerance interval was generated in order to define a statistical method for determining whether a particular marker was lost in any individual sample. More specifically, using the pooled variance from 20 loci it was determined that the experimental ΔCt values followed a normal distribution pattern according to a Shapiro-Wilk W test for normality. The pooled standard deviation (0.12) of 7 normal SJL mice (4 female and three male) from these loci (d.f.=140) were used to calculate a tolerance interval for the analysis of mouse chromosome 2 in which 95% of the time with 95% confidence a given measurement for an individual mouse would be scored a value of two copies if the measured value fell in the range of 1.48–2.52. A value lower than 1.48 was given an integer score of 1 and a value greater than 2.52 was given an integer score of 3. FIG. 6 shows the results of the assay determinations, with highlighted regions showing the regions of loss.

Figure 7A:
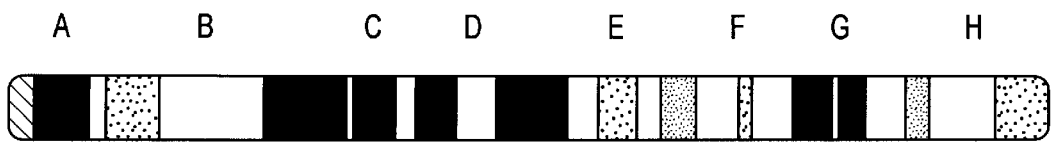
FIGS. 7A–7D present CGH profiles of chromosome 2 from 3 SJL mice as compared to results obtained using the methods of the present invention. In each panel (FIGS. 7B–7D), the dark line in the center of the two lighter lines is the measured red to green ratios, the lighter lines above and below are plus and minus one standard deviation. The circles at the bottom of each figure represent the approximate position of the markers tested using the methods of the present inventions. Filled circles (●) indicate loci that were measured to be present at 2 DNA copies and blank circles (○) indicate loci measured to be present at 1 DNA copy.
Figure 7B:
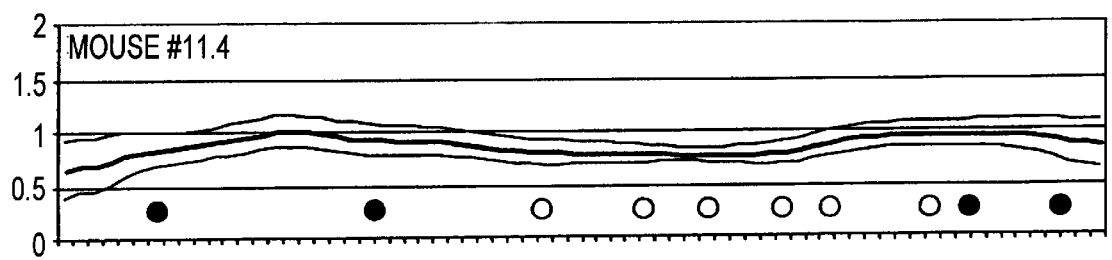
Figure 7C:
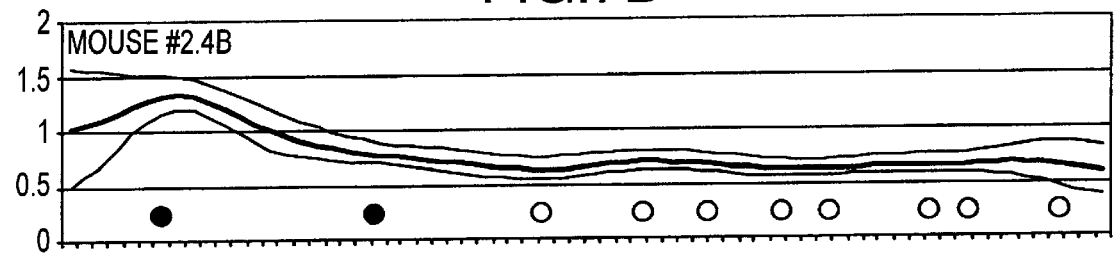
Figure 7D:
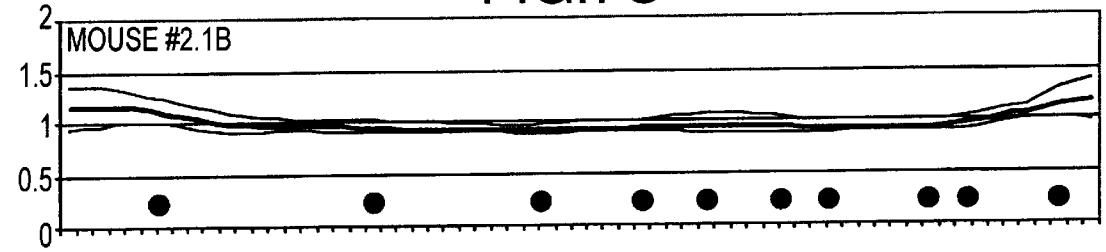

CGH analysis was performed on DNA from spleens of three of the irradiated mice, two with leukemia (#11.4 and #2.4B—FIGS. 7B and 7C, respectively) and one without (#2.1B—FIG. 7D). The CGH results show chromosome 2 copy number losses in the two leukemic mice and no loss in the non-leukemic mouse. By comparing the regions of loss in FIG. 6 and FIGS. 7B to 7D, it can be seen that the two analytical procedures are in complete agreement as to regions of loss.

FISH analysis was performed on BACs containing DNA from the spleens of three other irradiated mice, two with leukemia (#2.5 and #12.2) and one without (#8.5). These BACs contained DNA from the proximal (BAC356), mid-region (BAC62), and the distal (BAC415) segment of mouse chromosome 2. These three BAC clones were selected and mapped to chromosome 2 by PCR with STS primer pairs. DNA from each BAC was fluorescently labeled, hybridized to metaphase spreads of spleen cells from each mouse, and the number of fluorescent spots in a large number of cells were enumerated by fluorescence microscopy.

Results of the FISH analysis are shown in Table III below; Table III also lists the map position of each clone. The FITC (Fluorescein isothiocyanate) to TR (Texas Red) ratio indicates the relative number of copies of each BAC in the number of nuclei indicated; the ratio is similar to that obtained with the methods of the present invention wherein the average copy number of a locus is measured. A ratio of about 1 indicates that there is an equal number of copies at these loci. A ratio of approximately 0.5 indicates that there is only half the number of copies of one locus. For example, the ratio of 0.5 when the mid-chromosomal region (BAC62) is compared with the proximal chromosomal region (BAC356) for mice 12.2 and 2.5 indicates that there is only one-half the number of copies of BAC62 as compared to BAC356 for these two mice.

These FISH data support the findings obtained for the copy number values obtained using the assay method of Example I which show that mice 12.2 and 2.5 have one copy of chromosome 2, which contains an interstial deletion. Comparison of the results obtained by the methods of the present invention (see FIG. 6 and FIGS. 7B–7D) with the FISH results in Table III, also demonstrates that the two analytical procedures are in complete agreement as to regions of loss.

Thus, this study demonstrated the utility of the methods of the present invention for localizing a region of deletion in radiation-induced leukemia in inbred SJL mice. The region defined by this analytical technique is similar to that found by cytogenetic and LOH analyses (26, 27). Hence, the methods of the present invention provide a fast and high-resolution tool for mapping regions of deletion in inbred mouse strains, obviating the need for expensive and time consuming backcross breeding.

TABLE III

| Mouse sample | # of nuclei | # of signals FITC | # of signals Texas Red | Ratio (FITC:TR) |
|---|---|---|---|---|
| 8.5** | n = 150 | Bac62 | Bac356 | |
| | | 291 | 268 | 1.09 |
| 12.2* | n = 150 | Bac62 | Bac356 | |
| | | 153 | 289 | 0.53 |
| | n = 150 | Bac415 | Bac356 | |
| | | 292 | 286 | 1.02 |
| 2.5* | n = 96 | Bac62 | Bac356 | |
| | | 103 | 171 | 0.60 |
| | n = 74 | Bac415 | Bac356 | |
| | | 142 | 139 | 1.02 |

*Leukemic
**Non-Leukemic

EXAMPLE VIII

Reproducibility of Results

Using the assay described in Example I, the DNA copy number measurements of several loci on mouse chromosome 2 were repeated three times in order to assess the repeatability of the methods of the present invention (Table IV). A total of 13 markers were tested on 4 DNAs. However, only data for the markers D2MIT9 and D2MIT65 are shown because they span a breakpoint of a regional DNA loss in one of the mouse leukemia samples, 2.4B.

Three mice, 2.1B, 2.2B and 2.5B, retained both copies of all markers tested. The range of values for copy number was from 1.70 to 2.27 DNA copies, all within the 95% tolerance interval. The average standard deviation of all measurements was 0.16 DNA copies. The average coefficient of variation for all unknown markers on all DNAs was 11.4%±5.7%. The range for two copies was from 2 to 22% (data not shown).

In mouse 2.4B, the average measurement at the D2MIT9 locus in three separate experiments was 1.04±0.11 DNA copies. A students T-test using these data compared to that of normal SJL mice, indicates that this value is significantly different from 2 (P<0.0001). This value indicates that this marker was lost and that the breakpoint for the deletion in this mouse is located between the markers D2MIT9 and D2MIT65.

TABLE IV

|  | Expt. a | Expt. b | Expt. c | DNA copy # Ave | Std Dev | T-test |
|---|---|---|---|---|---|---|
| Mouse 2.1B | | | | | | |
| D2mit65 | 2 | 2.09 | 1.83 | 1.70 | 1.87 | 0.20 | 0.29559735 |
| D2mit9 | 2 | 1.99 | 1.77 | 1.81 | 1.86 | 0.12 | 0.10442598 |
| Mouse 2.2B | | | | | | |
| D2mit65 | | 2.08 | 1.78 | 1.80 | 1.89 | 0.17 | 0.28975204 |
| D2mit9 | | 2.27 | 1.96 | 1.76 | 2.00 | 0.26 | 0.97442298 |
| Mouse 2.4B | | | | | | |
| D2mit65 | | 2.02 | 1.66 | 1.63 | 1.77 | 0.22 | 0.10620455 |
| D2mit9 | | 1.17 | 1.01 | 0.95 | 1.04 | 0.11 | 4.1844E-05 |
| Mouse 2.5 | | | | | | |
| D2mit65 | | 2.02 | 1.83 | 1.74 | 1.86 | 0.14 | 0.17422554 |
| D2mit69 | | 2.15 | 1.89 | 1.71 | 1.92 | 0.22 | 0.50032835 |

Although the foregoing invention has been described in detail for purposes of clarity and understanding, it will be obvious to those with skill in the art that certain modifications can be practiced within the scope of the appended claims. All publications and patent documents cited above are hereby incorporated by reference in their entirety for all purposes to the same extent as if each were so individually denoted.

REFERENCES

1. Botstein D, W. R., Skolnick M, Davis R W. Construction of a genetic linkage map in man using restriction fragment length polymorphisms., Am J Hum Genet. 32: 314–31, 1980.
2. Aldridge J, K. L., Bruns G, Tantravahi U, Lalande M, Brewster T, Moreau and E, W. M., Bromley W, Roderick T, and Latt, S. A. A strategy to reveal high-frequency RFLPs along the human X chromosome., Am J Hum Genet. 36: 546–64, 1984.
3. Jeffreys A J, W. V., Thein S L Individual-specific 'fingerprints' of human DNA., Nature. 316: 76–9, 1985.
4. Weber and J L Informativeness of human (dC-dA)n.(dG-dT)n polymorphisms., Genomics. 7: 524–30, 1990.
5. Cawkwell L, B. S., Lewis F A, Dixon M F, Taylor G R, Quirke P Rapid detection of allele loss in colorectal tumours using microsatellites and fluorescent DNA technology., Br J Cancer. 67: 1262–7, 1993.
6. Ziegle J S, S. Y., Corcoran K P, Nie L, Mayrand P E, Hoff L B, McBride L J, Kronick M N, Diehl S R Application of automated DNA sizing technology for genotyping microsatellite loci., Genomics. 14: 1026–31, 1992.
7. Gross D S, G. W. The ubiquitous potential Z-forming sequence of eucaryotes, (dT-dG)n.(dC-dA)n, is not detectable in the genomes of eubacteria, archaebacteria, or mitochondria., Mol Cell Biol. 6: 3010–3, 1986.
8. Litt M, L. J. A hypervariable microsatellite revealed by in vitro amplification of a dinucleotide repeat within the cardiac muscle actin gene., Am J Hum Genet. 44: 397–401, 1989.
9. Hamada H, P. M., Kakunaga T A novel repeated element with Z-DNA-forming potential is widely found in evolutionarily diverse eukaryotic genomes., Proc Natl Acad Sci USA. 79: 6465–9, 1982.
10. Beckman J S, W. J. Survey of human and rat microsatellites., Genomics. 12: 627–31, 1992.
11. Nagase H, B. S., Cordell H, Kemp C J, Fee F, Balmain A Distinct genetic loci control development of benign and malignant skin tumours in mice., Nat Genet. 10: 424–9, 1995.
12. Heid, C. A., Stevens, J., Livak, K. J., and Williams, P. M. Real time quantitative PCR., Genome Research,. 6: 986–994, 1996.
13. Collins C, R. J., Kowbel D, Godfrey T, Tanner M, Hwang S I, Polikoff D, Nonet G, Cochran J, Myambo K, Jay K E, Froula J, Cloutier T, Kuo W L, Yaswen P, Dairkee S, Giovanola J, Hutchinson G B, Isola J, Kallioniemi O P, Palazzolo M, Martin and C, E. C., Pinkel D, Gray J W, et al Positional cloning of ZNF217 and NABC1: genes amplified at 20q13.2 and overexpressed in breast carcinoma., Proc Natl Acad Sci USA. 95: 8703–8, 1998.
14. Kallioniemi A, K. O., Piper J, Tanner M, Stokke T, Chen L, Smith H S, Pinkel D, Gray J W, Waldman F M Detection and mapping of amplified DNA sequences in breast cancer by comparative genomic hybridization., Proc Natl Acad Sci USA. 91: 2156–60, 1994.
15. Gibson, U. E. M., Heid, C. A. and Williams, P. M. A novel method for real time quantitative RT-PCR., Genome Research. 6: 995–1001, 1996.
16. Holland, P. M., Abramson, R. D., Watson, R. and Gelfand, D. H. Detection of specific polymerase chain reaction product by utilizing the 5'-3' exonuclease activity of Thermus aquaticus DNA polymerase., PNAS. 88: 7276–7280, 1991.
17. Livak, K. J., Flood, S. J., Marmaro, J., Giusti, W. and Deetz, K. Oligonucleotides with fluorescent dyes at opposite ends provide a quenched probe system useful for detecting PCR product and nucleic acid hybridization., PCR Methods and Applications 357–362, 1995.
18. Hahn, G. a. W. M. Statistical Intervals; a guide for practitioners, p. p 311: John Wiley & Sons. New York, N.Y., 1991.
19. Pierce J C, S. N., Sauer B A mouse genomic library in the bacteriophage P1 cloning system: organization and characterization., Mamm Genome. 3: 550–8, 1992.
20. Stokke T, C. C., Kuo W L, Kowbel D, Shadravan F, Tanner M, Kallioniemi A, Kallioniemi O P, Pinkel D, Deaven L, et al A physical map of chromosome 20 established using fluorescence in situ hybridization and digital image analysis., Genomics. 26: 134–7, 1995.
21. Pinkel, D., Straume, T. and Gray, J. W. Cytogenetic analysis using quantitative, high sensitivity, fluorescence hybridization., Proc. Natl. Acad. Sci. USA. 83: 2934–2938., 1986.
22. Johnson G D, D. R., McNamee K C, Russell G, Goodwin D, Holborow Fading of immunofluorescence during microscopy: a study of the phenomenon and its remedy., EJ J Immunol Methods. 55: 231–42, 1982.
23. Kallioniemi, A., Kallioniemi, O.-P., Sudar, D., Rutovitz, D., Gray, J. W., Waldman, F. and Pinkel, D. Comparative genomic hybridization for molecular cytogenetic analysis of solid tumors., Science. 258: 818–21, 1992.
24. Piper J, R. D., Sudar D, Kallioniemi A, Kallioniemi O P, Waldman F M, Gray J W, Pinkel D Computer image analysis of comparative genomic hybridization., Cytometry. 19: 10–26, 1995.
25. Tanner M M, T. M., Kallioniemi A, Isola J, Kuukasjarvi T, Collins C, Kowbel D, Guan X Y, Trent J, Gray J W, Meltzer P, Kallioniemi O P Independent amplification and frequent co-amplification of three nonsyntenic regions on the long arm of chromosome 20 in human breast cancer., Cancer Res. 56: 3441–5, 1996.
26. Clark D J, M. E., Bouffler S D, Huiskamp R, Skidmore C J, Cox R, Silver A R Microsatellite analysis of recurrent chromosome 2 deletions in acute myeloid leukaemia induced by radiation in F1 hybrid mice., Genes Chromosomes Cancer. 16: 238–46, 1996.
27. Alexander B J, R. J., Morahan G, Cook W D Gene deletion explains both in vivo and in vitro generated chromosome 2 aberrations associated with murine myeloid leukemia., Leukemia. 9: 2009–15, 1995.

What is claimed is:

1. A method of measuring copy number of a polynucleotide locus in a sample, comprising:

(a) amplifying a test polynucleotide locus in a nucleic acid sample from a test subject and determining a value for the quantity of the test locus in the sample from the test subject;

(b) amplifying a plurality of reference polynucleotide loci in a second nucleic acid sample from the test subject and determining a value for the quantity of the reference loci in the second sample from the test subject;

(c) amplifying the test polynucleotide locus in a nucleic acid sample from a control subject and determining a value for the quantity of the test locus in the sample from the control subject;

(d) amplifying a plurality of reference polynucleotide loci from a second nucleic acid sample from the control subject and determining a value for the quantity of the reference loci in the second sample from the control subject; and (e) determining a measure of the copy number of the test locus in the sample from the test subject from the values for the test locus and the reference loci in the test subject and from the values of the test locus and the reference loci in the control subject.

2. A method according to claim 1, wherein (a) the value for the test locus in the test subject is a value for the extent of amplification required for amplification product of the test locus to reach a threshold level;

(b) the value for the reference loci in the test subject is a value for the extent of amplification required for amplification product of the reference loci to reach the threshold level;

(c) the value for the test locus in the control subject is a value for the extent of amplification required for amplification product of the test locus in the control subject to reach the threshold level; and (d) the value for the reference loci in the control subject is a value for the extent of amplification required for amplification product of the reference loci in the control subject to reach a threshold level.

3. A method according to claim 1, wherein the plurality of reference loci in the nucleic acid sample from the test subject are amplified simultaneously, and wherein the plurality of reference loci in the control subject are amplified simultaneously.

4. A method according to claim 1, wherein at least some of the reference loci comprise a common nucleotide segment.

5. A method according to claim 4, wherein the common nucleotide segment comprises a simple sequence repeat.

6. A method according to claim 5, wherein the simple sequence repeat is a CA repeat.

7. A method according to claim 1, wherein at least some of the reference loci comprise different sequences.

8. The method according to claim 1, wherein the test locus and the reference loci comprise a common nucleotide segment.

9. The method according to claim 8, wherein the common nucleotide segment comprises a simple sequence repeat.

10. The method according to claim 9, wherein the simple sequence repeat is a CA repeat.

11. The method according to claim 1, wherein the test locus and the reference loci comprise different nucleotide sequences.

12. The method according to claim 1, wherein at least 3 reference loci are amplified in each of the test sample and the control sample.

13. The method according to claim 12, wherein 6–10 reference loci are amplified in each of the test sample and the control sample.

14. The method according to claim 1, wherein
(a) the amplifying steps are conducted in the presence of a label; and
(b) the values for the test locus and the reference loci in the test subject and the values for the test locus and the reference loci for the control subject are determined by measuring a signal from a complex formed between the label and the amplification products.

15. The method according to claim 1, wherein
(a) the amplifying steps are conducted in the presence of a labeled probe which is complimentary to the amplification products; and
(b) the values for the test locus and the reference loci in the test subject and the values for the test locus and the reference loci for the control subject are determined by measuring a signal from the labeled probe or fragments thereof.

16. The method according to claim 15, wherein the signal is generated from a conformational change in the labeled probe.

17. The method according to claim 15, wherein the amplifying steps are conducted in the presence of a nucleic acid polymerase having a 5'-3' nuclease activity which digests the labeled probe.

18. The method according to claim 17, wherein the labeled probe comprises a label, the label being selected from the group consisting of fluorescent dyes, chromophores, radioisotopes, electron dense reagents, enzymes and ligands having specific binding partners.

19. The method according to claim 15, wherein the labeled probe comprises two labels.

20. The method according to claim 19, wherein the two labels are fluorescent dyes.

21. The method according to claim 20, wherein one fluorescent dye is a reporter dye and the other dye is a quenching dye.

22. The method according to claim 21, wherein the reporter dye is selected from the group consisting of 6-carboxy fluorescein (FAM), 2',4',5',7',-tetrachloro-4,7-dichlorofluorescein (TET), and 2',7'-dimethoxy-4',5'-6-carboxyrhodamine (JOE).

23. The method according to claim 21, wherein the quenching dye is selected from the group consisting of 6-carboxy tetramethyl rhodamine (TAMRA), and (4-dimethylamine)azobenzene sulfonic acid (DABSYL).

24. The method according to claim 17, wherein the signal is a fluorescence emission that is generated as the labeled probe is digested by the 5'-3' nuclease activity of the nucleic acid polymerase.

25. The method according to claim 21, wherein the probe has the structure reporter dye-TGTGTGTGTGTGTGTGTGTGT-quenching dye (SEQ ID NO:2).

26. The method according to claim 25, wherein the reporter dye is 6-carboxy fluorescein (FAM) and the quenching dye is 6-carboxy tetramethyl rhodamine (TAMRA).

27. The method according to claim 15, wherein the labeled probe is at least 10 nucleotides long.

28. The method according to claim 2, wherein the threshold level is at least 10 standard deviations above a baseline value, the baseline value being the magnitude of the signal detectable prior to the formation of products.

29. The method according to claim 1, wherein the test subject has symptoms of a disease, has a known susceptibility to a disease, or has neither symptoms nor a known susceptibility to disease.

30. The method according to claim 29, wherein the test subject is suspected of having cancer or has cancer.

31. The method according to claim 29, wherein the disease is selected from the group consisting of Wolf-Hirschorn, cri du chat, Williams, Trisomy 8, Duplication 9, Prader-Willi/Angelman, Miller-Dieker, DiGeorge/velocardiofacial/Shprintzen disease.

32. The method according to claim 1, wherein the test subject is a human fetus.

33. The method according to claim 1, wherein
(a) the value for the test locus in the test subject is the number of amplification cycles necessary for amplification product of the test locus to reach the threshold value and is designated Ct (test marker);
(b) the value for the reference loci in the test subject is the number of amplification cycles necessary for amplification products of the reference loci to reach the threshold value and is designated Ct (test pooled reference);
(c) the value for the test locus in the control subject is the number of amplification cycles necessary for amplification product of the test loci in the control subject to reach the threshold value and is designated Ct(calibrator test marker);
(d) the value for the reference loci in the control subject is the number of amplification cycles necessary for amplification products of the reference loci in the control subject to reach the threshold value and is designated Ct(calibrator pooled reference); and
(e) the step of determining a measure of the copy number of the test locus in the test subject is calculated from the values for Ct(test marker), Ct(test pooled reference), Ct(calibrator test marker), and Ct(calibrator pooled reference).

34. The method according to 33, wherein the step of determining a measure of the copy number of the test locus in the test sample further comprises, determining a difference value, $\Delta Ct$(calibrator DNA), for the control subject by calculating a difference between the value for the test locus in the control subject, Ct(calibrator test marker), and the value for the reference loci in the control subject, Ct(calibrator pooled reference), according to the equation $$\Delta Ct\text{(calibrator DNA)} = Ct\text{(calibrator test marker)} - Ct\text{(calibrator pooled reference)},$$

and wherein the measure of the copy number of the test locus in the test subject is determined from the values for Ct(test marker), Ct(test pooled reference), and ΔCt (calibrator DNA).

35. The method according to claim 34, wherein the values for Ct(test marker), Ct(test pooled reference) and ΔCt (calibrator DNA) are mean values, mean Ct(test marker), mean Ct(test pooled reference) and mean ΔCt(calibrator DNA), respectively.

36. The method according to claim 35, wherein the mean ΔCt(calibrator DNA) value is determined from the Ct(calibrator test marker) and Ct(calibrator pooled reference) values for at least 5 different individuals.

37. The method according to claim 36, wherein the mean ΔCt(calibrator DNA) value is determined from the Ct(calibrator test marker) and Ct(calibrator pooled reference) values for 5–10 different individuals.

38. The method according to claim 35, wherein the step of determining a measure of the copy number of the test locus in the test sample further comprises, (a) determining a difference value for the test subject, ΔCt(test DNA), by calculating a difference between the mean value for the test subject, mean Ct(test marker), and the mean value for the reference loci in the test subject, mean Ct(test pooled reference), according to the equation $$\Delta Ct(\text{test DNA}) = \text{mean } Ct(\text{test marker}) - \text{mean } Ct(\text{test pooled reference});$$

(b) determining a difference value, ΔΔCt, determined from the difference value for the test subject, ΔCt(test DNA), and the mean difference value for the multiple control subjects, mean ΔCt(calibrator DNA), according to the equation $$\Delta\Delta Ct = \Delta Ct(\text{test DNA}) - \text{mean } \Delta Ct(\text{calibrator DNA}); \text{ and}$$

(c) determining the measure of the copy number of the test locus in the sample from the value for ΔΔCt.

39. The method according to claim 38, wherein the step of determining a measure of the copy number for the test locus for test subjects in which the test locus is amplified further comprises (a) determining the efficiency, E, of amplification for the test locus; and (b) determining the relative copy number of the test locus according to the equation $$\text{Relative copy number in diploid genome} = 2(1+E)^{-\Delta\Delta Ct}.$$

40. The method according to claim 39, further comprising assessing whether the test individual has a disease or is susceptible to a disease, a relative copy number greater than 2 indicating that the test individual has the disease or is susceptible to the disease.

41. The method according to claim 40, wherein the test subject is a human fetus.

42. The method according to claim 38, wherein the step of determining a measure of the copy number for the test locus for test subjects is calculated according to the equation $$\text{Relative copy number in a diploid genome} = 2(2^{-\Delta\Delta Ct}).$$

43. The method according to claim 42, further comprising assessing whether the test individual has a disease or is susceptible to a disease, a relative copy number less than 2 indicating that the test individual has the disease or is susceptible to the disease.

44. The method according to claim 43, wherein the test subject is a human fetus.

45. A method of measuring copy number of a polynucleotide locus in a sample, comprising (a) amplifying a test polynucleotide locus in a nucleic acid sample from a test subject and determining a value for the quantity of the test locus in the sample from the test subject;

(b) amplifying a plurality of reference polynucleotide loci in a second nucleic acid sample from the test subject and determining a value for the quantity of the reference loci in the second sample from the test subject; and (c) determining a measure of the copy number of the test locus in the sample from the test subject from the values for the test locus and the reference loci in the test subject and from a value of the test locus and a value for reference loci in a control subject, wherein the value for the test locus in the control subject is a value for the quantity of the test locus in a sample from the control subject, and wherein the value for the reference loci in the control subject is a value for the quantity of the reference loci in a second sample from the control subject.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:TM-TaqMan
      dual-labeled fluorogenic oligonucleotide probe
      complementary to amplification products of
      CA-repeat
<221> NAME/KEY: modified_base
<222> LOCATION: (1)
<223> OTHER INFORMATION: 5'-t attached to 6-carboxy fluorescein (FAM)
<221> NAME/KEY: modified_base
<222> LOCATION: (21)
<223> OTHER INFORMATION: 3'-t attached to 6-carboxy tetramethyl
      rhodamine (TAMRA)

<400> SEQUENCE: 1
ngtgtgtgtg tgtgtgtgtg n                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:TM-TaqMan
      dual-labeled fluorogenic oligonucleotide probe
      complementary to amplification products of
      CA-repeat
<221> NAME/KEY: modified_base
<222> LOCATION: (1)
<223> OTHER INFORMATION: 5'-t attached to reporter dye
<221> NAME/KEY: modified_base
<222> LOCATION: (21)
<223> OTHER INFORMATION: 3'-t attached to quenching dye

<400> SEQUENCE: 2
ngtgtgtgtg tgtgtgtgtg n                                              21